(12) United States Patent
Jones et al.

(10) Patent No.: US 8,372,819 B2
(45) Date of Patent: Feb. 12, 2013

(54) METHODS AND COMPOSITIONS FOR TARGETING SKIP

(75) Inventors: Katherine Jones, Solana Beach, CA (US); Lirong Zhang, San Diego, CA (US); Vanessa Bres, San Diego, CA (US); Yupeng Chen, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 13/078,813

(22) Filed: Apr. 1, 2011

(65) Prior Publication Data

US 2011/0269819 A1 Nov. 3, 2011

Related U.S. Application Data

(60) Provisional application No. 61/322,890, filed on Apr. 11, 2010.

(51) Int. Cl.
*A61K 48/00* (2006.01)

(52) U.S. Cl. ...... 514/44; 536/24.5; 536/24.31; 536/24.1

(58) Field of Classification Search .................. None
See application file for complete search history.

(56) References Cited

U.S. PATENT DOCUMENTS

2008/0207549 A1* 8/2008 Nakamura et al. .............. 514/44

OTHER PUBLICATIONS

Chen et al. (Cancer Research 63, 6626-6634, Oct. 2003).*
Prathapam et al., (Nucleic Acids Research 2002, vol. 30, No. 23: 5261-5268).*
Chen 2009. (Pigment Cell Melanoma Res. 2009, 22; 761-772).*
Weinstein et al. (Nature Clinical Practice Oncology 2006, vol. 3: 448-457).*

* cited by examiner

*Primary Examiner* — Kimberly Chong
(74) *Attorney, Agent, or Firm* — Kilpatrick Townsend & Stockton LLP

(57) ABSTRACT

Provided herein are methods and compositions for modulating apoptosis by targeting SKIP (Ski-interacting protein) activity. Methods of increasing DNA damage-induced cell death in cancer cells, and reducing DNA damage-induced cell death in normal cells are provided.

12 Claims, 9 Drawing Sheets

SEQUENCE LISTING

<160> NUMBER OF SEQ ID NOS: 52

<210> SEQ ID NO 1
<211> LENGTH: 536
<212> TYPE: PRT
<213> ORGANISM: Homo sapiens

<400> SEQUENCE: 1

Met Ala Leu Thr Ser Phe Leu Pro Ala Pro Thr Gln Leu Ser Gln Asp
1               5                   10                  15

Gln Leu Glu Ala Glu Glu Lys Ala Arg Ser Gln Arg Ser Arg Gln Thr
            20                  25                  30

Ser Leu Val Ser Ser Arg Arg Glu Pro Pro Pro Tyr Gly Tyr Arg Lys
        35                  40                  45

Gly Trp Ile Pro Arg Leu Leu Glu Asp Phe Gly Asp Gly Gly Ala Phe
    50                  55                  60

Pro Glu Ile His Val Ala Gln Tyr Pro Leu Asp Met Gly Arg Lys Lys
65                  70                  75                  80

Lys Met Ser Asn Ala Leu Ala Ile Gln Val Asp Ser Glu Gly Lys Ile
                85                  90                  95

Lys Tyr Asp Ala Ile Ala Arg Gln Gly Gln Ser Lys Asp Lys Val Ile
            100                 105                 110

Tyr Ser Lys Tyr Thr Asp Leu Val Pro Lys Glu Val Met Asn Ala Asp
        115                 120                 125

Asp Pro Asp Leu Gln Arg Pro Asp Glu Glu Ala Ile Lys Glu Ile Thr
    130                 135                 140

Glu Lys Thr Arg Val Ala Leu Glu Lys Ser Val Ser Gln Lys Val Ala
145                 150                 155                 160

Ala Ala Met Pro Val Arg Ala Ala Asp Lys Leu Ala Pro Ala Gln Tyr
                165                 170                 175

Ile Arg Tyr Thr Pro Ser Gln Gln Gly Val Ala Phe Asn Ser Gly Ala
            180                 185                 190

Lys Gln Arg Val Ile Arg Met Val Glu Met Gln Lys Asp Pro Met Glu
        195                 200                 205

Pro Pro Arg Phe Lys Ile Asn Lys Lys Ile Pro Arg Gly Pro Pro Ser
    210                 215                 220

Pro Pro Ala Pro Val Met His Ser Pro Ser Arg Lys Met Thr Val Lys
225                 230                 235                 240

Glu Gln Gln Glu Trp Lys Ile Pro Pro Cys Ile Ser Asn Trp Lys Asn
                245                 250                 255

Ala Lys Gly Tyr Thr Ile Pro Leu Asp Lys Arg Leu Ala Ala Asp Gly
            260                 265                 270

Arg Gly Leu Gln Thr Val His Ile Asn Glu Asn Phe Ala Lys Leu Ala

```
             275                 280                 285
Glu Ala Leu Tyr Ile Ala Asp Arg Lys Ala Arg Glu Ala Val Glu Met
        290                 295                 300
Arg Ala Gln Val Glu Arg Lys Met Ala Gln Lys Glu Lys Glu Lys His
305                 310                 315                 320
Glu Glu Lys Leu Arg Glu Met Ala Gln Lys Ala Arg Glu Arg Arg Ala
                325                 330                 335
Gly Ile Lys Thr His Val Glu Lys Glu Asp Gly Glu Ala Arg Glu Arg
            340                 345                 350
Asp Glu Ile Arg His Asp Arg Arg Lys Glu Arg Gln His Asp Arg Asn
        355                 360                 365
Leu Ser Arg Ala Ala Pro Asp Lys Arg Ser Lys Leu Gln Arg Asn Glu
    370                 375                 380
Asn Arg Asp Ile Ser Glu Val Ile Ala Leu Gly Val Pro Asn Pro Arg
385                 390                 395                 400
Thr Ser Asn Glu Val Gln Tyr Asp Gln Arg Leu Phe Asn Gln Ser Lys
                405                 410                 415
Gly Met Asp Ser Gly Phe Ala Gly Gly Glu Asp Glu Ile Tyr Asn Val
            420                 425                 430
Tyr Asp Gln Ala Trp Arg Gly Gly Lys Asp Met Ala Gln Ser Ile Tyr
        435                 440                 445
Arg Pro Ser Lys Asn Leu Asp Lys Asp Met Tyr Gly Asp Asp Leu Glu
    450                 455                 460
Ala Arg Ile Lys Thr Asn Arg Phe Val Pro Asp Lys Glu Phe Ser Gly
465                 470                 475                 480
Ser Asp Arg Arg Gln Arg Gly Arg Glu Gly Pro Val Gln Phe Glu Glu
                485                 490                 495
Asp Pro Phe Gly Leu Asp Lys Phe Leu Glu Glu Ala Lys Gln His Gly
            500                 505                 510
Gly Ser Lys Arg Pro Ser Asp Ser Ser Arg Pro Lys His Glu His
        515                 520                 525
Glu Gly Lys Lys Arg Arg Lys Glu
    530                 535

<210> SEQ ID NO 2
<211> LENGTH: 56
<212> TYPE: DNA
<213> ORGANISM: Artificial Sequence
<220> FEATURE:
<223> OTHER INFORMATION: Synthetic oligonucleotide primer

<400> SEQUENCE: 2
aatctggaca aggacatgta tggcgacgat ctcgaagcca gaataaagac caacag    56

<210> SEQ ID NO 3
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 3
cttgtggagc cggagct                                                17

<210> SEQ ID NO 4
<211> LENGTH: 20
<212> TYPE: DNA
<213> ORGANISM: Artificial Sequence
<220> FEATURE:
```

```
<223> OTHER INFORMATION: Synthetic oligonucleotide

<400> SEQUENCE: 4
tggtgtctcg gtgacaaagt                                              20

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
tggcggacga cctcaacg                                                18

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
ccctgggtaa gggcaggag                                               19

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
tcagcgcacg atcactgtc                                               19

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 8
ccagcaggca caacaccac                                               19

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
agctggaagt cgagtgtgct                                              20

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
tcctgagcag aagagtttgg a                                            21

<210> SEQ ID NO 11
```

```
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 11
gaaggtgaag gtcggagtc                                                     19

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
gaagatggtg atgggatttc                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
agcaggctgt ggctctgatt                                                    20

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 14
caaaatagcc accagcctct tct                                                23

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 15
ctgtcctccc cgaggtca                                                      18

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
acatctcagg ctgctcagag tct                                                23

<210> SEQ ID NO 17
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 17
```

```
tatatcaggg ccgcgctg                                                    18

<210> SEQ ID NO 18
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 18
ggctccacaa ggaactgact tc                                               22

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 19
ccaggaaggg cgaggaaa                                                    18

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 20
gggaccgatc ctagacgaac tt                                               22

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21
agtcactcag ccctggagtc aa                                               22

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 22
ggagagtgag tttgcccatg a                                                21

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 23
cctcccacaa tgctgaatat acag                                             24

<210> SEQ ID NO 24
<211> LENGTH: 27
<212> TYPE: DNA
<213> ORGANISM: Artificial Sequence
<220> FEATURE:
```

```
<223> OTHER INFORMATION: Synthetic oligonucleotide

<400> SEQUENCE: 24
agtcactaag aatcatttat tgagcac                                              27

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 25
cactgcaatt tggcccaga                                                       19

<210> SEQ ID NO 26
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 26
gtgcagtaga gaattattcc acatttg                                              27

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
gcgagactgt ggccttgtgt                                                      20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
cgttccaggg tccacaaagt                                                      20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
tgtctggctc cgagtttgtg                                                      20

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
ggtcagaaac cccaacattc c                                                    21

<210> SEQ ID NO 31
```

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 31
cccgcattgc ttgcttatta a                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 32
gagcttcacc acatgcgttt c                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 33
gaagagcaaa tgagccaaac g                                              21

<210> SEQ ID NO 34
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 34
ggagcaaccg gcaaacg                                                   17

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
ggagactctc agggtcgaaa                                                20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
ggattagggc ttcctcttgg                                                20

<210> SEQ ID NO 37
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 37
```

-continued cagagcaggc aggtagg                                          17

<210> SEQ ID NO 38
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 38
tttcccaagg atgtcgt                                          17

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 39
ccagggcctt ccttgtatct ct                                    22

<210> SEQ ID NO 40
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 40
acatccccag ccggttct                                         18

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 41
ctggagactc tcagggtcga a                                     21

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
cacatgtccg cacctgtcat                                       20

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
ccccactgtc ttcctcagtt g                                     21

<210> SEQ ID NO 44
<211> LENGTH: 21
<212> TYPE: DNA
<213> ORGANISM: Artificial Sequence
<220> FEATURE:

-continued

<223> OTHER INFORMATION: Synthetic oligonucleotide

<400> SEQUENCE: 44
agaagtcagc caggccaaga a                                              21

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
ggtggtcccc acttagcaca                                                20

<210> SEQ ID NO 46
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 46
gcaatcctct gccactccc                                                 19

<210> SEQ ID NO 47
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 47
ccgggcagtg gttgaggg                                                  18

<210> SEQ ID NO 48
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 48
ggccagtgag cgcagaagc                                                 19

<210> SEQ ID NO 49
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 49
ccgatcccag catccct                                                   17

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 50
gccggaagtt cagtttgtct c                                              21

<210> SEQ ID NO 51

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 51
ggaagtggtg cattgcaaat g                                              21

<210> SEQ ID NO 52
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 52
cacacaagcg ccagagaca                                                 19
```

METHODS AND COMPOSITIONS FOR TARGETING SKIP

CROSS-REFERENCES TO RELATED APPLICATIONS

This application claims priority to U.S. Provisional Appl. No. 61/322,890, filed Apr. 11, 2010, the disclosure of which is incorporated herein by reference in its entirety.

STATEMENT AS TO RIGHTS TO INVENTIONS MADE UNDER FEDERALLY SPONSORED RESEARCH OR DEVELOPMENT

The invention was made with Government support under Grant No. CA125535 awarded by the National Institutes of Health. The Government has certain rights in the invention.

BACKGROUND OF THE INVENTION

Factors that regulate the elongation phase of RNA polymerase II (RNAPII) transcription also play an important role in protecting cells from DNA damage and environmental stress. Inhibition of transcription elongation activates the p53 tumor suppressor to signal a stress response, even in the absence of DNA damage (Derheimer. et al., *Prot Natl Acad Sci* 104:12778-12783 (2007); Gartel, Biochim Biophys Acta 1786:83-86 (2008)). Flavopiridol (FP) promotes apoptosis through induction of p53 and inhibition of short-lived anti-apoptotic proteins, and is currently in clinical trials as an anti-cancer agent for leukemia and solid tumors (Canduri et al., Med Chem 4:210-218 (2008); Wang et al., *Mini Rev Med Chem* 9:379-385 (2009)). Thus, RNAPII is a genome wide sensor for DNA damage, through its ability to activate p53 and initiate programmed cell death upon encountering significant blocks to elongation.

The Ski-interacting protein SKIP (Snw1 and NCoA62) is a transcriptional coactivator for many newly induced genes (Leong et al. 2001, 2004; Zhang et al. 2003; Folk et al. 2004; MacDonald et al. 2004) and counteracts transcriptional repression by retinoblastoma (Prathapam et al. 2002). The SKIP homologs in *Saccharomyces cerevisiae* (Prp45) and *Drosophila* (BX42) are essential for cell viability, splicing (Ambrozkova et al., *Biochem Biophys Res Common* 284: 1148-1154 (2001); Makarov et al., *Science* 298: 2205-2208 (2002); Gahura et al., *J Cell Biochem* 106:139-151 (2009)), and nuclear export of spliced mRNAs (Farny et al., *Genes Dev* 22:66-78 (2008)). Although elongation factors can affect splicing indirectly through changes in the rate of elongation, and defects in cotranscriptional splicing can reduce RNAPII elongation rates in vivo (Kornblihtt *Adv Exp Med Biol* 623: 175-189 (2007); Pirngruber et al., *Cell Cycle* 8:3636-3642 (2009)), SKIP is recruited to promoters as well as transcribed regions and appears to play a direct role in each process.

Different subsets of p53 target genes specify whether cells will arrest to repair DNA damage, or undergo apoptosis (Vazquez et al., *Nat Rev Drug Discov* 7:979-987 (2008); Vousden et al., *Cell* 137:413-431 (2009)). Key p53 target genes in these opposing pathways are the anti-apoptotic G1 cell cycle arrest factor p21 (Abbas & Dutta, *Nat Rev Cancer* 9:400-414 (2009)) and the proapoptotic BH3-only Bcl-2 protein PUMA. The relative levels of these two proteins help to determine the extent of cell survival in response to DNA damage (Yu & Zhang, *Cancer Cell* 4:248-249 (2003); Iyer et al., *Proc Natl Acad Sci* 101:7386-7391 (2004)). Known transcription factors that impact this balance include c-Myc, which represses p21 without affecting PUMA expression (Seoane et al., *Nature* 419: 729-734 (2002); Jung et al., *Cell Cycle* 8: 982-989 (2009)), and the bromodomain protein Brd7, which promotes p53 binding to the p21, but not PUMA, gene (Drost et al., *Nat Cell Bio* 112:380-391 (2010)). Cell growth arrest arising from rapid p21 induction is an initial protective response to DNA damage or oncogene expression. Although the p21 gene is predominantly regulated at the level of transcription, additional factors control its translation as well as protein and mRNA stability.

Cancer is widely recognized as one of the major challenges to the healthcare industry, in terms of the variety of specific disease processes embraced by the term, the number of people and animals afflicted, and the effort and resources devoted to its treatment. For years, cancer has resisted attempts to understand and control the disease. The major, broad-based therapeutic approaches to cancer treatment continue to be burdened by deleterious side effects. For example, chemotherapy involves the delivery of cytotoxic compounds that target dividing cells to thereby destroy cancer cells. Healthy dividing cells are also lost, however, and the treatments can lead to serious, life-threatening complications. The treatments frequently result in pain, nausea, hair loss, and a highly increased risk of serious infection. Radiotherapy, another broad-based approach, also imperfectly targets cancer cells, with the result that healthy as well as cancerous cells can receive a lethal dose of radiation, leading to side effects such as pain, loss of vigor, and an increased risk of secondary malignancies, up to 20%, in some cases.

The inventors have discovered a novel target for preferentially inducing cell death in cancer (or pre-cancer) cells, or preferentially reducing DNA damage-induced cell death in non-cancer cells. Thus, provided herein is a broad-based therapeutic strategy for addressing cancer and the side effects of existing cancer treatments.

BRIEF SUMMARY OF THE INVENTION

The inventors have shown that basal and stress-induced p21 expression requires the SKIP/SNW1 transcription elongation and splicing factor. These results were unexpected, given that p53 induction of p21 does not require the P-TEFb elongation factor, and that neither P-TEFb nor SKIP is required for stress-induced transcription in other contexts (Brès et al., *Mol Cell* 36:75-87 (2009)). The inventors have also shown that reducing SKIP expression results in increased p53 expression, and increased cell death (p53-mediated apoptosis). Apoptosis is increased dramatically in the presence of an agent that increases p53-mediated apoptosis, such as DNA damage.

Accordingly, provided herein is a valuable new target for cancer therapy. In some embodiments, the invention provides methods of treating cancer in an individual said method comprising administering to the individual an effective amount of a SKIP inhibitor, thereby treating the cancer in the individual.

In some embodiments, the SKIP inhibitor is selected from the group consisting of anti-SKIP antisense (e.g., siRNA, shRNA, RNAi, etc.), flavopiridol, an anti-SKIP antibody or aptamer, a dominant negative SKIP protein, an inhibitor of DHX8, an inhibitor of PPIL1, and an inhibitor of Prp19. In some embodiments, the inhibitor of DHX8, PPIL1, or Prp19 is an RNAi inhibitor, or an agent that inhibits interaction with SKIP.

In some embodiments, the cancer is a leukemia or other non-solid cancer that has relatively high p53 expression. In some embodiments, the cancer has relatively low p53 expression or activity, e.g., a solid tumor, such as prostate cancer, ovarian cancer, breast cancer, colorectal cancer, lung cancer, pancreatic cancer, throat cancer, brain cancer, etc.

In some embodiments, the individual is further treated with an effective amount of an agent that induces (increases, activates, agonizes) p53-mediated apoptosis. In some embodiments, the agent is a DNA damaging agent. In some embodiments, the DNA damaging agent is selected from a chemotherapeutic drug and radiotherapy. In some embodiments, the administration and treatment are concurrent. In some embodiments, the administration and treatment are sequential, e.g., with exposure to the DNA damaging agent occurring before administration of the SKIP inhibitor, or after administration of the SKIP inhibitor.

In some embodiments, the invention provides methods of selectively inducing apoptosis in a cell comprising contacting the cell with an inhibitor of Ski-interacting protein (SKIP) in the cell, thereby selectively inducing apoptosis in a cell. In some embodiments, the SKIP inhibitor is selected from the group consisting of SKIP-specific RNAi (e.g., siRNA, shRNA, etc.), flavopiridol, a SKIP-specific antibody or aptamer, a dominant negative SKIP protein, an inhibitor of DHX8, an inhibitor of PPIL1, and an inhibitor of Prp19.

In some embodiments, the cell is further treated with an agent that induces p53-mediated apoptosis. In some embodiments, the agent is a DNA damaging agent, e.g., selected from a chemotherapeutic drug and radiotherapy. In some embodiments, the contacting and treatment are concurrent. In some embodiments, the contacting and treatment are sequential.

In some embodiments, the contacting is in vitro. In some embodiments, the cell is a cancer cell, e.g., a non-solid cancer cell, or a cell from a solid tumor, e.g., a cell that forms part of a solid tumor. In some embodiments, the contacting is in vivo, i.e., in an individual. In some embodiments, the individual has cancer e.g., a non-solid cancer (e.g., leukemia, lymphoma, myeloma) or a solid tumor. In some embodiments, the SKIP inhibitor is administered locally to the site of the cancer.

Further provided are methods for identifying an inhibitor of SKIP comprising: (i) contacting a cell with a candidate inhibitor; (ii) determining the level of SKIP activity, wherein a reduced level of SKIP activity compared to a standard control indicates that the candidate inhibitor is an inhibitor of SKIP, thereby identifying an inhibitor of SKIP. In some embodiments, the SKIP activity is SKIP expression. In some embodiments, the SKIP activity is selected from binding to DHX8, binding to Prp19, binding to PPIL1, binding to p53, binding to U2AF65, binding to p21 mRNA, inducing p21 expression, and reducing apoptosis (i.e., so that a SKIP inhibitor would selectively induce apoptosis). In some embodiments, the standard control is a cell that is not contacted with a candidate inhibitor.

Also provided are methods of reducing apoptosis in a population of cells, comprising contacting the population with a SKIP agonist, thereby reducing apoptosis in the population. In some embodiments, the population of cells is treated with (exposed to) an agent that induces p53-mediated apoptosis. In some embodiments, the agent is a DNA damaging agent, e.g., selected from a chemotherapeutic drug and radiotherapy. In some embodiments, the population of cells are non-cancer cells. In some embodiments, the SKIP agonist is an expression vector comprising a polynucleotide encoding SKIP.

In some embodiments, the contacting is in vitro. In some embodiments, the contacting is in vivo, i.e., in an individual. In some embodiments, the individual has cancer. In some embodiments, the SKIP agonist is associated with (e.g., directly or indirectly attached to, e.g., in a liposome) a targeting agent to target non-cancer cells.

DETAILED DESCRIPTION OF THE INVENTION

I. Introduction

Figure 1:
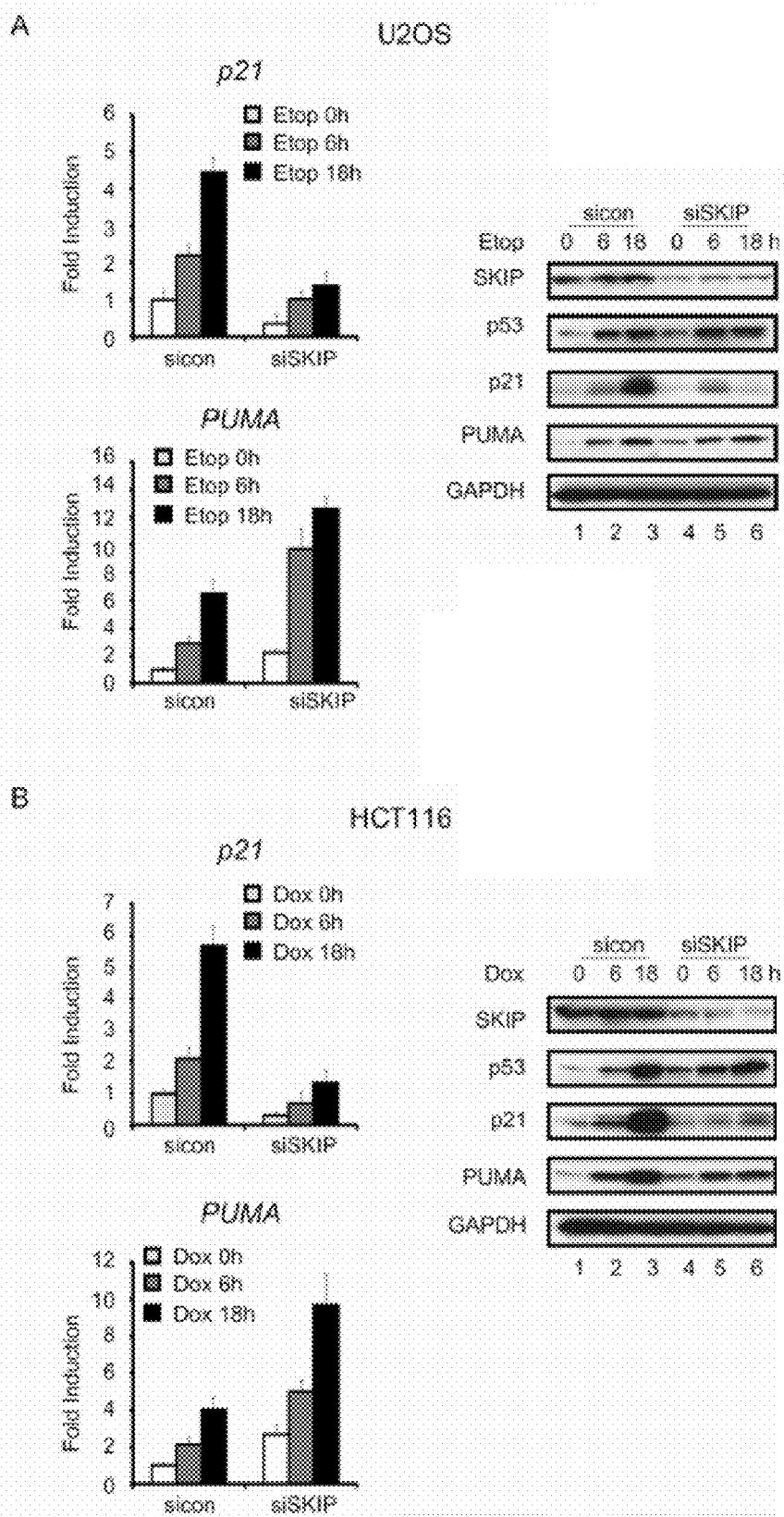
FIG. 1. SKIP is required for DNA damage-induced p21 gene expression. (A) qRT-PCR analysis of p21 (top panel) and PUMA (bottom panel) mRNA levels. U2OS cells were transfected with control (sicon) or SKIP siRNA (siSKIP) for 48 h, and incubated in the presence or absence of etoposide (20 μM) for the indicated times. (Right panel, lanes 1-6) Protein lysates were subjected to immunoblot analysis. (B) qRT-PCR analysis of p21 (top panel) and PUMA (bottom panel) mRNA levels. HCT116 cells were transfected with control or SKIP siRNA for 48 h, and incubated in the presence or absence of doxorubicin (0.5 μM) for the indicated times. (Right panel, lanes 1-6) Protein lysates were subjected to immunoblot analysis. All of the mRNA expression levels were normalized to GAPDH mRNA, and the values represent the fold increase or decrease over untreated cells. Error bars represent the standard deviation obtained from three independent experiments.

The Ski-interacting protein SKIP/SNW1 functions as both a splicing factor and a transcriptional coactivator for induced genes. Transcription elongation factors such as SKIP are dispensable in cells subjected to DNA damage stress. However, SKIP is shown herein to be critical for both basal and stress-induced expression of the cell cycle arrest factor p21$^{Cip1}$. RNAi chromatin immunoprecipitation (RNAi-ChIP) and RNA immunoprecipitation (RNA-IP) experiments indicate that SKIP is not required for transcription elongation of the gene under stress, but instead is critical for splicing and p21$^{Cip1}$ protein expression. Together, the results described herein define a new step that controls cancer cell apoptosis.

The inventors have thus discovered an unusual mechanism for p21 gene expression that involves gene-specific splicing by SKIP and is essential for cancer cell survival under stress. In particular, SKIP is shown herein to be critical for splicing and expression of p21, but not for PUMA or other investigated p53 target genes, in human colon cancer and osteosarcoma cells. SKIP associates with the 3' splice site recognition factor U2AF65, but not U2AF35, and recruits it to the p21 gene and mRNA in vivo. In contrast, U2AF65 recruitment and splicing at the PUMA gene is independent of SKIP. As a consequence, siRNA-mediated depletion of SKIP induces p53-dependent apoptosis, which is most pronounced in cells subjected to DNA damage. The results also reveal that cancer cell survival upon DNA damage also depends on SKIP and associated factors (DHX8, PPIL1, and Prp 19) that function as gene-specific regulators of p21 mRNA splicing.

II. Definitions

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

"Cancer", "tumor," "transformed" and like terms include precancerous, transformed, and cancerous cells, and can refer to a solid tumor, or a non-solid cancer (see, e.g., Edge et al. *AJCC Cancer Staging Manual* (7th ed. 2009); Cibas and Ducatman *Cytology: Diagnostic principles and clinical correlates* (3rd ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, *Culture of Animal Cells a Manual of Basic Technique* (3rd ed. 1994)). Although transformation can arise from infection with a transforming virus and incorporation of new genomic DNA, or uptake of exogenous DNA, it can also arise spontaneously or following exposure to a carcinogen.

The term "cancer" thus refers cancers and carcinomas, sarcomas, adenocarcinomas, lymphomas, leukemias, solid and lymphoid cancers, etc. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma. In some embodiments, the compositions and methods of the present invention are useful for treating cancer.

A "cancer target" or "cancer marker" is a molecule that is differentially expressed or processed in cancer, e.g., on a cancer cell or in the cancer milieu. Exemplary cancer targets are cell surface proteins (e.g., cell adhesion molecules, receptors), intracellular receptors, hormones, and molecules such as proteases that are secreted by cells into the cancer mileu.

In some embodiments, the cancer target can be associated with a certain type of cancer cell, e.g., non-small cell lung cancer cells, prostate cancer, colorectal cancer, breast cancer or ovarian cancer. A cell type specific target is typically expressed at levels at least 2 fold greater in that cell type than in a reference population of cells. In some embodiments, the cell type specific marker is present at levels at least 3, 4, 5, 6, 7, 8, 9,10 20, 50, 100, or 1000 fold higher than its average expression in a reference population. Thus, the target can be detected or measured to distinguish the cell type or types of interest from other cells.

The term "SKIP" refers to the 536 amino acid human protein (SEQ ID NO:1), species homologues, variants (e.g., naturally-occurring genetic variants), and fragments of SKIP that retain at least one SKIP activity. Functionally active fragments (domains) of SKIP are listed on the NCBI Gene entry for SKIP, found on the NCBI website at ncbi.nlm.nih.gov/gene/22938. The term can also be used to refer to SKIP-encoding polynucleotides, and genomic sequences associated with SKIP.

"SKIP activities" include but are not limited to: mediating p21 expression in stress conditions (e.g., DNA damage); reducing cell death in stress conditions (as compared to cell death in the absence of SKIP); binding to p21 mRNA; binding to SKIP associated proteins; and transcriptional co-activation.

A "SKIP associated protein," "SKIP associated factor," "SKIP interacting protein," "SKIP interacting factor," and like terms refer to factors that associate with SKIP and mediate SKIP activities. Examples of SKIP associated proteins include DHX8, Prp19, PPIL1, U2AF65, p53, and c-Myc.

An agent that induces or increases p53-mediated apoptosis can include agents that increase p53 expression or activity (e.g., stress inducing agents), agents that reduce degradation of p53 (e.g., nutlin), and DNA damaging agents (e.g., various chemotherapeutics, radioactive agents, and radiotherapy).

A "DNA damaging agent," as used herein, refers to agents or conditions that either directly alter DNA structure or indirectly allow DNA damage to occur. Examples of DNA damaging agents include reactive oxygen species, UV radiation, x-ray and gamma radiation, naturally occurring and synthetic mutagenic chemicals (e.g., DNA intercalators), etc.

An agent that "selectively induces apoptosis" increases the level apoptosis as compared to the level of apoptosis in the absence of the agent. For example, p53 induces both apoptosis and DNA repair mechanisms. Selective induction of apoptosis indicates that the level of apoptosis is augmented, i.e., that the cell is predisposed to apoptosis, as opposed to DNA repair and survival.

"Apoptosis" is often referred to as programmed cell death. Apoptosis is marked by characteristic changes, including blebbing, loss of cell membrane potential, cell shrinkage, nuclear fragmentation, and chromatin condensation. Apoptosis can be distinguished from necrosis by the presence of self-contained apoptotic bodies that are engulfed and removed by surrounding cells.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, *Molecular Cloning: A Laboratory Manual,* 18.1-18.88).

The term "transfection" or "transfecting" is defined as a process of introducing a nucleic acid molecule to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures well known in the art.

Expression of a transfected gene can occur transiently or stably in a host cell. During "transient expression" the transfected nucleic acid is not integrated into the host cell genome, and is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The terms "identical" or percent "identity," in the context of two or more nucleic acids, or two or more polypeptides, refer to two or more sequences or subsequences that are the same or have a specified percentage of nucleotides, or amino acids, that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the compliment of a nucleotide test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The sensitivity of the hybridization assays may be enhanced through use of a nucleic acid amplification system that multiplies the target nucleic acid being detected. Amplification can also be used for direct detection techniques. Examples of such systems include the polymerase chain reaction (PCR) system and the ligase chain reaction (LCR) system. The selected sequences can be generally amplified using, for example, nonspecific PCR primers and the amplified target region later probed for a specific sequence indicative of a mutation. It is understood that various detection probes, including Taqman® and molecular beacon probes can be used to monitor amplification reaction products in real time.

The term "antisense" is used herein as a general term referring to RNA targeting strategies for reducing gene expression. Antisense includes RNAi, siRNA, shRNA, etc. Typically, the antisense sequence is identical to the targeted sequence (or a fragment thereof), but this is not necessary for effective reduction of expression. For example, the antisense sequence can have 85, 90, 95, 98, or 99% identity to the complement of a target RNA or fragment thereof. The targeted fragment can be about 10, 20, 30, 40, 50, 10-50, 20-40, 20-100, 40-200 or more nucleotides in length.

The term "RNAi" refers to RNA interference strategies of reducing expression of a targeted gene. RNAi technique employs genetic constructs within which sense and anti-sense sequences are placed in regions flanking an intron sequence in proper splicing orientation with donor and acceptor splicing sites. Alternatively, spacer sequences of various lengths can be employed to separate self-complementary regions of sequence in the construct. During processing of the gene construct transcript, intron sequences are spliced-out, allowing sense and anti-sense sequences, as well as splice junction sequences, to bind forming double-stranded RNA. Select ribonucleases then bind to and cleave the double-stranded RNA, thereby initiating the cascade of events leading to degradation of specific mRNA gene sequences, and silencing specific genes. The phenomenon of RNA interference is described and discussed in Bass, *Nature* 411: 428-29 (2001); Elbahir et al., *Nature* 411: 494-98 (2001); and Fire et al., *Nature* 391: 806-11 (1998); and WO 01/75164, where methods of making interfering RNA also are discussed.

The term "siRNA" refers to small interfering RNAs, that are capable of causing interference with gene expression and can cause post-transcriptional silencing of specific genes in cells, for example, mammalian cells (including human cells) and in the body, for example, in a mammal (including humans). The siRNAs based upon the sequences and nucleic acids encoding the gene products disclosed herein typically have fewer than 100 base pairs and can be, e.g., about 30 bps or shorter, and can be made by approaches known in the art, including the use of complementary DNA strands or synthetic approaches. The siRNAs are capable of causing interference and can cause post-transcriptional silencing of specific genes in cells, for example, mammalian cells (including human cells) and in the body, for example, in a mammal (including humans). Exemplary siRNAs have up to 40 bps, 35 bps, 29 bps, 25 bps, 22 bps, 21 bps, 20 bps, 15 bps, 10 bps, 5 bps or any integer thereabout or therebetween. Tools for designing optimal inhibitory siRNAs include that available from DNAengine Inc. (Seattle, Wash.) and Ambion, Inc. (Austin, Tex.).

A "short hairpin RNA" or "small hairpin RNA" is a ribonucleotide sequence forming a hairpin turn which can be used to silence gene expression. After processing by cellular factors the short hairpin RNA interacts with a complementary RNA thereby interfering with the expression of the complementary RNA.

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "dominant negative protein" is a modified form of a wild-type protein that adversely affects the function of the wild-type protein within the same cell. As a modified version of a wild-type protein the dominant negative protein may carry a mutation, a deletion, an insertion, a post-translational modification or combinations thereof. Any additional modifications of a nucleotide or polypeptide sequence known in the art are included. The dominant-negative protein may interact with the same cellular elements as the wild-type protein thereby blocking some or all aspects of its function. For example, a dominant negative SKIP protein can interact with SKIP associated proteins, but not with p21 mRNA. The dominant negative SKIP would thus not allow for p21 expression, e.g., in response to DNA damage.

The term "antibody" refers to a polypeptide comprising a framework region from an immunoglobulin gene or fragments thereof that specifically bind and recognize an antigen, e.g., SKIP, p21, a particular cancer-associated marker, or any desired target. Typically, the "variable region" contains the antigen-binding region of the antibody (or its functional equivalent) and is most critical in specificity and affinity of binding. See Paul, *Fundamental Immunology* (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

The term "modulator" refers to agents that either increase or decrease activity or expression of a desired target. A "modulator of SKIP" or "modulator of SKIP activity" refers to an agent that increases or decreases SKIP expression or activity directly or indirectly and includes those molecules identified using in vitro and in vivo assays for SKIP expression, mRNA binding, transcriptional activity, and apoptosis.

The terms "agonist," "activator," "inducer" and like terms refer to molecules that increase activity or expression as compared to a control. Agonists are agents that, e.g., bind to, stimulate, increase, activate, enhance activation, sensitize or upregulate the activity of the target. The expression or activity can be increased 10%, 20%, 30%, 40%, 50%, 60%, 70%, 80%, 90% 100% or more than that in a control. In certain instances, the activation is 1.5-fold, 2-fold, 3-fold, 4-fold, 5-fold, 10-fold, or more in comparison to a control.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control.

An "inhibitor of SKIP," "SKIP antagonist," and like terms refer to an agent that reduces SKIP activity or expression relative to a standard control. SKIP antagonists include but are not limited to siRNA and other anti-SKIP antisense agents; anti-SKIP antibodies; agents that compete for binding to SKIP with known SKIP-associated factors, such as DHX8, Prp19, PPIL1, and U2AF65; agents that interfere with SKIP binding to p21 mRNA; dominant negative SKIP proteins; and small molecules as described herein.

An "activator of SKIP," "SKIP agonist," and like terms refer to an agent that increases SKIP activity or expression relative to a standard control. SKIP activity can be increased, e.g., by contacting the SKIP polypeptide with an agonist, or by increasing SKIP expression in a cell.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications, e.g., testing the activity of various SKIP modulators. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The terms "therapy," "treatment," and "amelioration" refer to any reduction in the severity of symptoms. In the case of treating cancer, treatment can refer to, e.g., reducing tumor size, number of cancer cells, growth rate, metastatic activity, reducing cell death of non-cancer cells, reduced nausea and other chemotherapy or radiotherapy side effects, etc. As used herein, the terms "treat" and "prevent" are not intended to be absolute terms. Treatment can refer to any delay in onset, amelioration of symptoms, improvement in patient survival, increase in survival time or rate, etc. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

In the context of the present invention, the effective amount of a SKIP inhibitor or agent that induces p53 mediated apoptosis (e.g., DNA-damaging agent) can change depending on whether these agents are administered in combination. Inhibition of SKIP can sensitize cells to p53 mediatedapoptosis, so that a lower dose of the SKIP inhibitor or agent that induces p53 mediated apoptosis will effectively induce apoptosis than when either agent is used alone.

The term "diagnosis" refers to a relative probability that cancer, as described herein, is present in the subject. Similarly, the term "prognosis" refers to a relative probability that a certain future outcome may occur in the subject. For example, in the context of the present invention, prognosis can refer to the likelihood that an individual will develop cancer, have recurrence, or the likely severity of the disease (e.g., severity of symptoms, rate of functional decline, survival, etc.). The terms are not intended to be absolute, as will be appreciated by any one of skill in the field of medical diagnostics.

"Biopsy" or "biological sample from a patient" as used herein refers to a sample obtained from a patient having, or suspected of having, cancer. In some embodiments, the sample may be a tissue biopsy, such as needle biopsy, fine needle biopsy, surgical biopsy, etc. The sample can comprise a tissue sample harboring the lesion or suspected lesion, although the biological sample may be also be derived from another site, e.g., a site of suspected metastasis, a lymph node, or from the blood. In some cases, the biological sample may also be from a region adjacent to the lesion or suspected lesion.

A "biological sample" can be obtained from a patient, e.g., a biopsy, from an animal, such as an animal model, or from cultured cells, e.g., a cell line or cells removed from a patient and grown in culture for observation. Biological samples include tissues and bodily fluids, e.g., blood, blood fractions, lymph, saliva, urine, feces, etc.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, *Bioconjugate Techniques* 1996, Academic Press, Inc., San Diego.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc. A "cancer patient" can refer to an individual that has been diagnosed with cancer, is currently following a therapeutic regimen, or is at risk of recurrence, e.g., after surgery to remove a tumor. In some embodiments, the cancer patient has been diagnosed with cancer and is a candidate for therapy. Cancer patients can include individuals that have not received treatment, are currently receiving treatment, have had surgery, and those that have discontinued treatment.

In the context of the present invention, e.g., methods of treating cancer, a subject in need of treatment can refer to an individual that has cancer or a pre-cancerous condition, has had cancer and is at risk of recurrence, is suspected of having cancer, is undergoing standard treatment for cancer, such as radiotherapy or chemotherapy, etc.

III. SKIP Polynucleotides and Polypeptides

SKIP (SKI-interacting protein) is a transcription elongation/splicing cofactor that is also referred to as SNW1, SNW domain containing 1, SKIIP, NCoA-62, homolog of drosophila BX42 and yeast Prp45. The protein and polynucleotide sequences of SKIP are known and publically available for many species (e.g., for human sequences, see UniProtein Number Q13573, RefSeq (mRNA) NM_012245, and Genbank No. AC008372 (NCoA-62)). SKIP, a member of the SNW gene family, is a transcriptional coactivator that enhances transcription from some Pol II promoters.

In some embodiments, SKIP is expressed in a cell, thereby increasing expression of SKIP in the cell. Alternatively, inhibitory polynucleotides, such as siRNA or antisense sequences, can be expressed in a cell to inhibit SKIP expression, as described in more detail below. In some cases, a polynucleotide encoding SKIP is introduced into a cell in vitro and the cell is subsequently introduced into a subject. In some cases, the cells are first isolated from the subject and then re-introduced into the subject after the polynucleotide is introduced. In some embodiments, SKIP-encoding polynucleotides or SKIP inhibitory polynucleotides are introduced directly into cells in the subject in vivo.

Conventional viral and non-viral based gene transfer methods can be used to introduce nucleic acids encoding engineered polypeptides of the invention in mammalian cells or target tissues. Such methods can be used to administer nucleic acids encoding SKIP polypeptides, or SKIP inhibitory polynucleotides to cells in vitro. In some embodiments, such polynucleotides are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds) (1995); and Yu et al., *Gene Therapy* 1:13-26 (1994).

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described, e.g., in U.S. Pat. No. 5,049,386, U.S. Pat. No. 4,946,787; and U.S. Pat. No. 4,897,355, and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

RNA or DNA viral based systems can be used to target the delivery of polynucleotides carried by the virus to specific cells in the body and deliver the polynucleotides to the nucleus. Viral vectors can be administered directly to patients (in vivo) or they can be used to transfect cells in vitro. In some cases, the transfected cells are administered to patients (ex vivo). Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism (target specificity) of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system can thus depend on the targeted cell type. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

Adenoviral based systems can also be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

Replication defective Adenoviral vectors (Ad vectors) have also become conventional for their large carrying capacity. An example of an Ad vector in a clinical trial involved polynucleotide therapy for antitumor immunization with intramuscular injection is described, e.g., in Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Recombinant adeno-associated virus vectors (rAAV), based on the defective and nonpathogenic parvovirus adeno-associated type 2 virus, can also be used for SKIP expression or inhibition. All vectors are derived from a plasmid that retains only the AAV 145 by inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

IV. Modulators of SKIP Expression and Activity

The results disclosed herein show that inhibition of SKIP activity reduces expression of p21 and increases cell death, especially in combination with highly elevated p53 activity (e.g., in the presence of a DNA damaging agent). Thus, provided herein are methods and compositions for modulating SKIP expression and/or activity in a mammalian cell by contacting the mammalian cell with a SKIP modulator. The SKIP modulator can be a small molecule modulator, a nucleic acid modulator (including aptamers), or an antibody. A SKIP modulator can be identified as an agent that has an effect on a SKIP activity. Assays for detecting SKIP activities are described in more detail below.

The SKIP modulator can be a SKIP agonist or a SKIP antagonist, as described herein. In some embodiments, the invention includes methods and compositions for activating SKIP, e.g., by increasing SKIP expression. In some embodiments, the SKIP agonist is an expression vector encoding SKIP, or encoding a SKIP-associated protein.

In some embodiments, the invention includes methods and compositions for inhibiting the expression, secretion, and/or activity of SKIP. The inventors have shown that inhibiting SKIP increases p53 levels, and thus can result in p53-mediated cell death. Exemplary SKIP inhibitors include siRNA and antisense, pRNA (promoter-associated RNA, see, e.g., Schmitz et al. (2010) *Genes Dev.* 24:2264-69), SKIP-specific antibodies and fragments thereof, and SKIP-specific aptamers. In some embodiments, SKIP activity can be inhibited, e.g., by inhibiting activity or expression of SKIP-associated proteins such as DHX8, PPIL1, and Prp19. The terms "inhibitor" and "antagonist" and like terms are used synonymously herein.

Thus, a nucleotide sequence that specifically interferes with expression of the SKIP gene (or the gene of a SKIP-associated protein such as DHX8, PPIL1, or Prp19) at the transcriptional or translational level can be used to treat or prevent pulmonary disease. This approach may utilize, for example, siRNA and/or antisense oligonucleotides to block transcription or translation of a specific mRNA (e.g., a genetic variant RNA), either by inducing degradation of the mRNA with a siRNA or by masking the mRNA with an antisense nucleic acid.

Double stranded siRNA that corresponds to the SKIP gene can be used to silence the transcription and/or translation by inducing degradation of SKIP mRNA transcripts, and thus treat cancer. The siRNA is typically about 5 to about 100 nucleotides in length, more typically about 10 to about 50 nucleotides in length, most typically about 15 to about 30 nucleotides in length. siRNA molecules and methods of generating them are described in, e.g., Bass, 2001, *Nature*, 411, 428-429; Elbashir et al., 2001, *Nature*, 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, *Molecular Interventions*, 2:158 (2002). For example, dsRNA oligonucleotides that specifically hybridize to the SKIP nucleic acid sequences described herein can be used in the methods of the present invention. A decrease in the severity of pulmonary disease symptoms in comparison to symptoms detected in the absence of the interfering RNA can be used to monitor the efficacy of the siRNA Antisense oligonucleotides that specifically hybridize to nucleic acid sequences encoding SKIP polypeptides can also be used to silence transcription and/or translation, and thus treat or prevent cancer. For example, antisense oligonucleotides that specifically hybridize to a SKIP polynucleotide sequence can be used. An increase in cell death, especially DNA damage induced cell death, in comparison to cell death detected in the absence of the antisense nucleic acids can be used to monitor the efficacy of the antisense nucleic acids.

Antisense nucleic acids are DNA or RNA molecules that are complementary to at least a portion of a specific mRNA molecule (see, e.g., Weintraub, *Scientific American,* 262:40 (1990)). Typically, synthetic antisense oligonucleotides are generally between 15 and 25 bases in length. Antisense nucleic acids may comprise naturally occurring nucleotides or modified nucleotides such as, e.g., phosphorothioate, methylphosphonate, and -anomeric sugar-phosphate, backbone-modified nucleotides.

In the cell, the antisense nucleic acids hybridize to the corresponding mRNA, forming a double-stranded molecule. The antisense nucleic acids, interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target nucleotide mutant producing cell. The use of antisense methods to inhibit the in vitro translation of genes is well known in the art (Marcus-Sakura, *Anal. Biochem.,* 172:289, (1988)). Less commonly, antisense molecules which bind directly to the DNA may be used.

Aptamers are nucleic acids that are designed to bind to a wide variety of targets in a non-Watson Crick manner. An aptamer can thus be used to detect, inhibit, or otherwise target nearly any molecule of interest, including a pulmonary disease associated protein. Methods of constructing and determining the binding characteristics of aptamers are well known in the art. For example, such techniques are described in U.S. Pat. Nos. 5,582,981, 5,595,877 and 5,637,459. Aptamers are typically at least 5 nucleotides, 10, 20, 30 or 40 nucleotides in length, and can be composed of modified nucleic acids to improve stability. Flanking sequences can be added for structural stability, e.g., to form 3-dimensional structures in the aptamer.

siRNA, antisense, and other nucleic acids can be delivered to the subject using any means known in the art, including by injection, inhalation, or oral ingestion. Another suitable delivery system is a colloidal dispersion system such as, for example, macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. Nucleic acids, including RNA and DNA within liposomes and be delivered to cells in a biologically active form (Fraley, et al., *Trends Biochem. Sci.,* 6:77, 1981). Liposomes can be targeted to specific cell types or tissues using any means known in the art.

The invention also provides antibodies that specifically bind to SKIP protein, or a SKIP-associated protein such as DHX8, PPIL1, or Prp19. Such antibodies can be used to sequester SKIP, e.g., to prevent p21 expression.

An antibody that specifically detects SKIP, or a SKIP-associated protein such as DHX8, PPIL1, or Prp19, can be isolated using standard techniques described herein. The protein sequences for these factors in a number of species, e.g., humans, non-human primates, rats, dogs, cats, horses, bovines, etc., are publically available.

Monoclonal antibodies are obtained by various techniques familiar to those skilled in the art. Briefly, spleen cells from an animal immunized with a desired antigen are immortalized, commonly by fusion with a myeloma cell (see, for example, Kohler & Milstein, *Eur. J. Immunol.* 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246: 1275-1281 (1989).

Monoclonal antibodies are collected and titered against SKIP (or a SKIP-associated protein) in an immunoassay, for example, a solid phase immunoassay with the immunogen immobilized on a solid support. Monoclonal antibodies will usually bind with a $K_d$ of at least about 0.1 mM, more usually at least about 1 µM, and can often be designed to bind with a $K_d$ of 1 nM or less.

The immunoglobulins, including SKIP-binding fragments and derivatives thereof, can be produced readily by a variety of recombinant DNA techniques, including by expression in transfected cells (e.g., immortalized eukaryotic cells, such as myeloma or hybridoma cells) or in mice, rats, rabbits, or other vertebrate capable of producing antibodies by well known methods. Suitable source cells for the DNA sequences and host cells for immunoglobulin expression and secretion can be obtained from a number of sources, such as the American Type Culture Collection (Catalogue of Cell Lines and Hybridomas, Fifth edition (1985) Rockville, Md).

In some embodiments, the antibody is a humanized antibody, i.e., an antibody that retains the reactivity of a non-human antibody while being less immunogenic in humans. This can be achieved, for instance, by retaining the non-human CDR regions that are specific for SKIP or SKIP-associated proteins, and replacing the remaining parts of the antibody with their human counterparts. See, e.g., Morrison et al., *PNAS USA,* 81:6851-6855 (1984); Morrison and Oi, *Adv. Immunol.,* 44:65-92 (1988); Verhoeyen et al., *Science,* 239:1534-1536 (1988); Padlan, *Molec. Immun.,* 28:489-498 (1991); Padlan, *Molec. Immun.,* 31(3):169-217 (1994). Techniques for humanizing antibodies are well known in the art and are described in e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) *Nature* 321: 522; and Verhoyen et al. (1988) *Science* 239:1534. Humanized antibodies are further described in, e.g., Winter and Milstein (1991) *Nature* 349:293. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

V. Methods for Identifying SKIP Modulators

The invention further provides methods for identifying modulators of SKIP expression, secretion, and/or activity. Methods for screening for or identifying SKIP antagonists can involve measuring the ability of the potential antagonists to reduce an identifiable SKIP activity or compete for binding with a known binding agent (e.g., a SKIP-specific antibody, or a SKIP interacting factor such as DHX8, PPIL1, Prp19, or U2AF65). For example, candidate agents can be screened for their ability to modulate p21 expression, modulate SKIP interaction with SKIP-associated factors, modulate SKIP expression, modulate cell death, e.g., in the presence of a DNA damaging agent, etc.

The screening methods of the invention can be performed as in vitro or cell-based assays. Cell based assays can be performed in any cells in which SKIP is expressed, either endogenously or through recombinant methods. Cell-based assays may involve whole cells or cell fractions containing SKIP to screen for agent binding or modulation of SKIP activity by the agent. Suitable cell-based assays are described in, e.g., DePaola et al., *Annals of Biomedical Engineering* 29: 1-9 (2001).

Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371:346), by following the incorporation of fluorescein-dUTP (Yonehara et al., 1989, J. Exp. Med. 169:1747). Apoptosis can also be assayed by acridine orange staining of tissue culture cells (Lucas et al., 1998, Blood 15: 4730-41). A test agent can be added to the apoptosis assay system and changes in induction of apoptosis relative to a control, e.g., where no test agent is added, can identify SKIP modulating agents. In some embodiments of the invention, an apoptosis assay can be used to test a candidate SKIP modulating agent that is initially identified using a cell-free assay system (e.g., to detect binding to a SKIP interacting protein, or a p21 polynucleotide). Apoptosis assays are described further in U.S. Pat. No. 6,133,437.

Cell cycling (e.g., as opposed to cell death) can be determined by detecting cell proliferation. Cell proliferation may be assayed via bromodeoxyuridine (BRDU) incorporation, which identifies a cell population undergoing DNA synthesis by incorporation of BRDU into newly-synthesized DNA. Newly-synthesized DNA can be detected using an anti-BRDU antibody (Hoshino et al., 1986, Int. J. Cancer 38:369; Campana et al., 1988, Immunol. Meth. 107:79), or by other means.

Cell proliferation can also be examined using [3H]-thymidine incorporation (Chen 1996, Oncogene 13: 1395-403; Jeoung 1995, J. Biol. Chem. 270: 18367-73). This assay also detects cells synthesizing DNA, by detecting incorporation of [3H]-thymidine into newly synthesized DNA. Incorporation can then be measured by standard techniques such as by counting of radioisotope in a scintillation counter (e.g., Beckman L S 3800 Liquid Scintillation Counter).

Cell proliferation may also be assayed by colony formation in soft agar (Sambrook et al., Molecular Cloning, Cold Spring Harbor (1989)). For example, cells transformed with SKIP are seeded in soft agar plates, and colonies are measured and counted after two weeks incubation. Cell cycling can also be assayed by flow cytometry (Gray et al. (1986) Int .J Radiat Biol Relat Stud Phys Chem Med 49: 237-55). For example, SKIP-expressing cells can be contacted with a test agent, stained with propidium iodide, and evaluated in a flow cytometer).

Assays for RNA binding or processing can be carried out as described in the Examples, or, e.g., based on homogeneous scintillation proximity (Liu et al., Anal Biochem 2001 289: 239-245), chemiluminescense (Mazumder Nucleic Acids Res 1998 26: 19962000), gel shift (Stull et al., Antisense Nucleic Acid Drug Dev 1996 6: 221-228; U.S. Pat. No. 6,004,749).

Electrophoretic mobility shift assay (EMSA or gel shift assay) is a powerful method for studying protein-DNA interactions. High throughput gel shift assays for nucleic acid binding can involve fluorescence-labeled oligodeoxynucleotide duplexes as specific probes and an automatic DNA sequencer for analysis (Ruscher et al., (2000) J Biotechnol 78: 163-70). High throughput methods can also involve colorimetric assays (Renard et al. (2001) Nucleic Acids Res 29 (4): E21), or homogeneous fluorescence assays for the detection and quantification of sequence-specific DNA-binding proteins (Heyduk and Heyduk (2001) Nat Biotechnol 20: 171-6).

DHX8, a SKIP interacting protein, is a helicase involved in unwinding double stranded DNA and RNA. An assay for determining DNA helicase activity can be used to detect the displacement of a radio-labeled oligonucleotide from single stranded DNA upon initiation of unwinding (Sivaraja et al, Anal Biochem (1998) 265: 22-27). An assay for RNA helicase activity relies on the scintillation proximity (SPA) assay to detect the displacement of a radio-labeled oligonucleotide from single stranded RNA (Kyono et al., Anal Biochem (1998) 257: 120-126). Additional assays are described, e.g., in 01/25487.

PPIL1 is a peptidyl-prolyl isomerase related to cyclophilin. Assays for detecting PPIL1 activity are described, e.g., in Janowski et al. (1997) *Anal Biochem* 15:252 and Nechama et al. (2009) *J Clin Invest* 119:3102.

Agents that are initially identified as SKIP modulators can be further tested to validate the apparent activity. Such studies can be conducted with suitable cell-based or animal models of cancer, e.g., xenotransplants in rodents. The basic format of such methods involves administering a lead compound identified during an initial screen to an animal that serves as a model and then determining if in fact the cell death of cancer cells is increased (or cell death of non-cancer cells is reduced). The animal models utilized in validation studies generally are mammals of any kind. Specific examples of suitable animals include, but are not limited to, primates (e.g., chimpanzees, monkeys, and the like) and rodents (e.g., mice, rats, guinea pigs, rabbits, and the like).

The agents tested as potential SKIP modulators can be any small chemical compound, or a biological entity, such as a polypeptide, sugar, nucleic acid or lipid. Alternatively, modulators can be genetically altered versions of SKIP, e.g., forms that do not bind DNA, or interact with other factors required for p21 expression. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays).

In some embodiments, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, and U.S. Pat. No. 5,288,514).

VI. Therapeutic Compositions and Methods

A. Conditions Amenable to Treatment

The invention includes methods of treating cancer, e.g., by inhibiting SKIP and increasing apoptosis in cancer cells. The term "cancer" refers to inappropriate cell proliferation, and encompasses a spectrum of neoplastic disorders, from precancerous dysplasias to multimodal metastases, that vary in treatment, prognosis, and curability.

Cancer cells can possess a number of characteristic properties such as uncontrolled proliferation, immortality, metastatic potential, rapid growth and proliferation rate, and certain typical morphological features. Cancer cells can be in the form of a tumor, but can also exist alone, or may be a non-tumor cancer cell, such as a leukemia cell. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer (e.g., CA125, PAP, PSA, CEA, AFP, HCG, CA 19-9, CA 15-3, CA 27-29, LDH, NSE, and others), and detecting a genotype indicative of a cancer (e.g., TP53, ATM, etc.). A negative result in one or more of the above detection methods does not necessarily indicate the absence of cancer, as a patient who has exhibited a complete response to a cancer treatment may still have a cancer, as evidenced by a subsequent relapse.

Once diagnosed, a cancer is usually "staged," a process which involves using the techniques of surgery, physical examination, histopathology, imaging, and laboratory evaluation to define the extent of disease and to divide the cancer patient population into groups according to probability of cure. Such systems are used both to plan treatment and determine the prognoses for the patient (Pazdur et al. *Cancer Patient Management: A Multidisciplinary Approach,* $12^{th}$ ed. 2009). The type or stage of the cancer can determine which therapeutic approaches to take, e.g., surgery, radiation therapy, and/or chemotherapy. For example, surgery can be used to remove a primary tumor, and remaining cells can be addressed with a SKIP modulator, e.g., in combination with chemotherapy and/or radiation.

Diseases or conditions of humans or other species which can be treated with a SKIP modulator, include, but are not limited to, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, and non-Hodgkin's lymphoma (see, CANCER:PRINCIPLES AND PRACTICE (DeVita, V. T. et al. eds 1997) for additional cancers).

B. DNA Damaging Agents

The compositions and methods of the invention focus on the amelioration and prevention (e.g., of recurrence) of cancer. Anti-cancer drugs including SKIP inhibitors, chemotherapy, antineoplastic agents, and radiotherapy can be used alone or in any combination, and can be combined with radiation and/or surgical therapies, as well as other conventional chemotherapeutic therapies or antibody therapies. The anti-cancer agent can also be combined with a diagnostic agent.

Chemotherapeutic agents include agents that interfere with mitosis and cell cycling, and agents that induce p53-mediated apoptosis, such as DNA damaging agents. Classes of chemotherapeutic agents include but are not limited to alkylating agents, antimetabolites, e.g, methotrexate, plant alkaloids, e.g., etoposide and vincristine, and antibiotics, e.g., doxorubicin as well as miscellaneous drugs that do not fall in to a particular class such as hydroxyurea. Other drugs include hormonal therapy.

Anti-cancer agents thus include agents that induce p53-dependent apoptosis (e.g., DNA damaging agents). Nutlin reduces p53 degradation, thus resulting in higher p53 levels and increased p53-mediated apoptosis. Examples of DNA damaging agents include plant alkaloids (e.g., etoposide, tenisopide, vinca alkaloids, irinotecan, topotecan), anthracyclines (e.g., doxorubicin, dounorubicin, epirubicin, idarubicin, valrubicin, mitoxantrone), 5-fluorouracil (5-FU), UV radiation, x-ray and gamma radiation, and radioactive emitters.

Anti-cancer agents can also include radionuclides for use in therapeutic applications. For example, emitters of Auger electrons, such as $^{111}$In, can be combined with a chelate, such as diethylenetriaminepentaacetic acid (DTPA) or 1,4,7,10-tetraazacyclododecane-1,4,7,10-tetraacetic acid (DOTA), and included in a targeted delivery composition, such as a liposome, to be used for treatment. Other suitable radionuclide and/or radionuclide-chelate combinations can include but are not limited to beta-emitting radionuclides ($^{177}$Lu, $^{153}$Sm, $^{88/90}$Y) with DOTA, $^{64}$Cu-TETA, $^{64}$Cu-DOTA, $^{188/186}$Re(CO)$_3$-IDA; $^{188/186}$Re(CO)triamines (cyclic or linear), $^{188/186}$Re(CO)$_3$-Enpy2, and $^{188/186}$Re(CO)$_3$-DTPA.

Radiation therapy also targets DNA, exploiting the fact that the radiation is more damaging to rapidly dividing cells than quiescent (non-cancer) cells. Radiation treatment, however, can lead to early and late radiation effects. The early effects can include erythema of the skin, desquamation, esophagitis, nausea, alopecia, and myelosuppression, while the late effects can include tissue necrosis and fibrosis. These side effects usually determine the limiting toxicity of radiation therapy. As explained herein, the compositions of the invention can be useful in minimizing radiation damage in non-cancer cells by expressing SKIP in non-cancer cells that may be affected by radiation.

Chemotherapeutic drugs that interfere with cell cycling and replication include platinum-based drugs, exemplified by cisplatin and oxaliplatin, and taxanes, exemplified by taxol. Platinum based drugs bind to DNA and interfere with replication. Taxanes act by interfering with cell division, thereby preventing growth of rapidly dividing cancer cells.

Chemotherapeutics thus include but are not limited to avastin, doxorubicin, cisplatin, oxaliplatin, carboplatin, 5-fluorouracil, gemcitibine or taxanes, such as paclitaxel and docetaxel.

The anti-cancer agent can be a platinum compound selected from cisplatin, carboplatin, ormaplatin, oxaliplatin, zeniplatin, enloplatin, lobaplatin, spiroplatin, ((−)-(R)-2-aminomethylpyrrolidine (1,1-cyclobutane dicarboxylato) platinum), (SP-4-3(R)-1,1-cyclobutane-dicarboxylato(2-)-(2-methyl-1,4-butanediamine-N,N')platinum), nedaplatin and (bis-acetato-ammine-dichloro-cyclohexylamine-platinum(IV)).

The anti-cancer agent can also be a vinca alkaloid selected from the group consisting of vincristine, vinblastine, vinleurosine, vinrodisine, vinorelbine and vindesine.

More than one anti-cancer agent can be combined, either in the same composition, or in separate compositions. The anti-cancer therapeutic agent(s) can also be combined with additional therapeutic agents as appropriate for the particular individual. Common therapeutic agents provided to cancer patients include medications to address pain, nausea, anemia, infection, inflammation, and other symptoms commonly experienced by cancer patients. In addition, the therapeutic agents can be delivered before, after, or with immune stimulatory adjuvants, such as aluminum gel or salt adjuvants (e.g., aluminum phosphate or aluminum hydroxide), calcium phosphate, endotoxins, toll-like receptor adjuvants and the like.

C. Pharmaceutical Compositions

A therapeutic agent used in the present invention can include any agent directed to treat cancer and cancer-related conditions or side effects in a subject. In general, any therapeutic agent known in the art can be used and formulated into a pharmaceutical composition, including without limitation agents listed in the United States Pharmacopeia (U.S.P.), *Goodman and Gilman's The Pharmacological Basis of Therapeutics*, 10$^{th}$ Ed., McGraw Hill, 2001; Katzung, Ed., *Basic and Clinical Pharmacology*, McGraw-Hill/Appleton & Lange, 8$^{th}$ ed., Sep. 21, 2000; *Physician's Desk Reference* (Thomson Publishing; and/or *The Merck Manual of Diagnosis and Therapy*, 18$^{th}$ ed., 2006, Beers and Berkow, Eds., Merck Publishing Group; or, in the case of animals, *The Merck Veterinary Manual*, 9$^{th}$ ed., Kahn Ed., Merck Publishing Group, 2005; all of which are incorporated herein by reference.

Therapeutic agents can be selected depending on the type of cancer to be treated. For example, certain types of cancers or tumors, such as carcinoma, sarcoma, leukemia, lymphoma, myeloma, and central nervous system cancers as well as solid tumors and mixed tumors, can involve administration the same or possibly different therapeutic agents. In certain embodiments, a therapeutic agent can be delivered to treat or affect a cancerous condition in a subject and can include chemotherapeutic agents, such as alkylating agents, antimetabolites, anthracyclines, alkaloids, topoisomerase inhibitors, and other anticancer agents.

In some embodiments, the agents can include antisense agents, microRNA, and/or siRNA agents. In this case, it can be desirable to deliver the expression vector specifically to a particular cell type. In some embodiments, a viral expression vector can be modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747-9751 (1995), reported that Moloney murine leukemia virus can be modified to express human heregulin fused to gp70, and the recombinant virus infects certain human breast cancer cells expressing human epidermal growth factor receptor. Similarly, other cancer cell targets can be targeted by including a targeting agent (e.g., antibody or ligand) on the viral expression vector. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Viral vectors can be delivered in vivo by administration to an individual, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., non-cancerous lymphocytes, bone marrow aspirates, tissue biopsy) or universal donor hematopoietic stem cells, followed by reimplantation of the cells into a patient, usually after selection for cells which have incorporated the vector.

The compositions disclosed herein can be administered by any means known in the art. For example, compositions may include administration to a subject intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intrathecally, subcutaneously, subconjunctival, intravesicularlly, mucosally, intrapericardially, intraumbilically, intraocularly, orally, locally, by inhalation, by injection, by infusion, by continuous infusion, by localized perfusion, via a catheter, via a lavage, in a creme, or in a lipid composition. Administration can be local, e.g., to a tumor site, or systemic.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

D. Administration

The suitability of a particular route of administration will depend in part on the pharmaceutical composition and its components and the cancer being treated. For example, treatment of tumors on the skin or on exposed mucosal tissue may be more effective if the composition is administered topically, transdermally, or mucosally (e.g., by nasal, sublingual, buccal, rectal, or vaginal administration). Treatment of tumors within the body, or prevention of metastasis, can be more effective with parenteral administration.

The invention provides methods of treating, preventing, and/or ameliorating a cancer in a subject in need thereof. The course of treatment is best determined on an individual basis depending on the particular characteristics of the subject and the type of treatment selected. The treatment can be administered to the subject on a daily, twice daily, bi-weekly, monthly or any applicable basis that is therapeutically effective. The treatment can be administered alone or in combination with a chemotherapeutic agent or radiotherapy. The chemotherapeutic agent or radiotherapy can be administered simultaneously with the SKIP modulator, at a different time, or on an entirely different therapeutic schedule (e.g., the SKIP modulator can be administered daily, while the chemotherapeutic agent or radiotherapy is weekly).

The dosage of a therapeutic agent administered to a patient will vary depending on a wide range of factors. For example, it would be necessary to provide substantially larger doses to humans than to smaller animals. The dosage will depend upon the size, age, sex, weight, medical history and condition of the patient, use of other therapies, the potency of the substance being administered, and the frequency of administration.

Having indicated that there is variability in terms of dosing, it is believed that those skilled in the art can determine appropriate dosing by administering relatively small amounts and monitoring the patient for therapeutic effect. If necessary, incremental increases in the dose can be made until the desired results are obtained. Generally, treatment is initiated with smaller dosages which may be less than the optimum dose of the therapeutic agent. Thereafter, the dosage is increased by small increments until the optimum effect under circumstances is reached. The total daily dosage can be divided and administered in portions during the day if desired.

Administration of a composition for treating cancer, e.g., by reducing SKIP activity, can be a systemic or localized administration. For example, treating a cancer patient can include administering a SKIP antagonist on a daily basis or otherwise regular schedule, e.g., in combination with a chemotherapeutic agent or radiotherapy.

The pharmaceutical preparation can be packaged or prepared in unit dosage form. In such form, the preparation is subdivided into unit doses containing appropriate quantities of the active component, e.g., according to the dose of the therapeutic agent. The unit dosage form can be a packaged preparation, the package containing discrete quantities of preparation. The composition can, if desired, also contain other compatible therapeutic agents.

The following discussion of the invention is for the purposes of illustration and description, and is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. All publications, patents, patent applications, Genbank numbers, and websites cited herein are hereby incorporated by reference in their entireties for all purposes.

VII. EXAMPLES

A. Materials and Methods

Plasmids, siRNAs, Drugs, and Antibodies

Mammalian expression constructs of human pV5-SKIP and pFlag-SKIP were generated by subcloning SKIP cDNA into pcDNA6 (Invitrogen) and pCMV-Tag2 (Stratagene) vectors, respectively. Human Flag-p21 was obtained from Addgene (plasmid no. 16240). The bacterial expression construct encoding full-length SKIP was described previously (Brès et al., *Mol Cell* 36:75-87 (2009)). For rescue experiments, siRNA-resistant vector was prepared by site-directed mutagenesis using the primer 5'-AATCTGGAC-AAGGA-CATGTATGGCGACGATCT CGAAGCCAGAATAAAGACCAACAG-3' (SEQ ID NO:2) with substituted nucleotides (underlined). The resultant cDNA fragment replaces the original nucleotide sequence targeted by SKIP siRNA without changing the amino acid sequence, and was subcloned into the pCMV-Tag2 vector. The mutations were confirmed by sequence analysis. Synthetic dsRNA oligonucleotides targeting SKIP, U2AF65, and CDK9 were purchased from Ambion and are listed in Table 1 below. Etopside, doxorubicin, Nutlin3, 5-FU, CHX, actinomycin D, and MG132 were purchased from Sigma, and TGF-β was obtained from R&D Systems. The antibodies for Western blots, ChIP, and RNA-IP are listed in Table 2 below.

TABLE 1

| Gene | Ambion siRNA ID # |
|---|---|
| SKIP | S22716 (mostly used), S22715, S22717 |
| CDK9 | S2834 |
| U2AF65 | S22364 |
| DHX8 | S4018 |
| PRP19 | S26185 |

TABLE 2

| Antibody | Company | Catalogue # |
|---|---|---|
| SKIP | Bethyl | A300-784A (WB) |
|  | Bethyl | A300-785A (ChIP and RNA-IP) |
| p53 (DO-1) | Santa Cruz | SC-126 |
| p53-S15P (16G8) | Cell Signaling | 9286 |
| HDM2 (Ab-1) | Calbiochem | OP46 |
| PUMA (Ab-1) | Calbiochem | PC686 |
| p21 (DCS60) | Cell Signaling | 2946 |
| Flag (M2) | Sigma | F1804 |
| Smad2/3 (FL-425) | Santa Cruz | SC-8332 |
| V5 | Invitrogen | 46-0705 |
| CDK9 (H-169) | Santa Cruz | SC-8338 |
| Spt5 (H-300) | Santa Cruz | SC-28678 |
| RNA Pol II (N20) | Santa Cruz | SC-899 |
| RNA Pol II H5 (Ser2) | Covance | MMS-129R |
| U2AF65 | Sigma | U4758 |
| U2AF35 | Bethyl | A302-079A |
| DHX8 | Bethyl | A300-626A |
| PRP19 | Bethyl | A300-101A |
| CBP80 | Mattaj lab |  |

Cell Lines and Cell Culture

U2OS, HCT116 (wild type, p21$^{-/-}$, and p53$^{-/-}$), H1299, HeLa, and MDA-MB-231 cells were maintained in DMEM supplemented with 10% FBS. The HCT116-SKIP stable cells were generated by transfecting the expression construct pV5-SKIP into the parental HCT116 cell line. Stable clones were selected in medium containing 10 μg/mL blasticidin (Invitrogen) for 3 wk.

Cell Cycle and Apoptosis Analysis

Cells were plated in 100-mm dishes and treated with the siRNAs, UV, or 5-FU. At the indicated time points, cells were trypsinized, washed with phosphate-buffered saline (PBS), and fixed in 70% ethanol overnight at 4° C. After being washed with PBS, cells were incubated with propidium iodide (PI)/RNase-staining buffer (BD Bioscience) for 15 min at room temperature. Cell distribution across the cell cycle was analyzed with FACS-can (Becton Dickinson) and CellQuest software. The apoptotic cells are represented in sub-G1 peaks on DNA histograms.

GST Pull-Down Experiments

SST fusion constructs were expressed in BL21 *Escherichia coli* cells, and crude bacterial lysates were prepared by sonication in GST lysis buffer (25 mM Tris at pH 7.5, 150 mM NaCl, 1 mM EDTA, protease inhibitor). Approximately 10 μg of the appropriate GST fusion proteins was incubated with precleared HCT116 nuclear extract for 2 h at 4° C. The binding reaction was then added with 30 μL of glutathione-Sepharose beads and mixed for another 1 h at 4° C. The beads were washed four times with the above GST lysis buffer, separated on a 10% SDS-PACE, and analyzed by Western blotting.

Subcellular Fractionation, qRT-PCR, and ChIP

Cell fractionation was performed using the PARIS kit (Ambion) according to the manufacturer's instructions. Total RNAs were isolated using Trizol and were subjected to DNaseI treatment prior to reverse transcription using random hexamers and Superscript III reverse transcriptase (Invitrogen). The resulting cDNAs were subjected to qPCR with the indicated primer sets (Table 3). Values were normalized to those of GAPDH. ChIP assays were performed essentially the same as described previously (Brès, V. et al., *Mol Cell* 36:75-87 (2009)), cells were fixed with 1% formaldehyde, and then whole-cell lysates were prepared.

TABLE 3

| Gene | Sense (5'-3') | SEQ ID NO: | Antisense (5'-3') | SEQ ID NO: |
|---|---|---|---|---|
| p21 | CTTGTGGAGCCGGAGCT | 3 | TGGTGTCTCGGTGACAAAGT | 4 |
| PUMA | TGGCGGACGACCTCAACG | 5 | CCCTGGGTAAGGGCAGGAG | 6 |
| GADD45 | TCAGCGCACGATCACTGTC | 7 | CCAGCAGGCACAACACCAC | 8 |
| NOXA | AGCTGGAAGTCGAGTGTGCT | 9 | TCCTGAGCAGAAGAGTTTGGA | 10 |
| GAPDH | GAAGGTGAAGGTCGGAGTC | 11 | GAAGATGGTGATGGGATTTC | 12 |

Protein lysate was subjected to ChIP with the indicated antibodies, followed by DNA purification. ChIP-enriched DNA was analyzed with qPCR with the indicated primer sets (Table 4).

TABLE 4

| | Sense (5'-3') | SEQ ID NO: | Antisense (5'-3') | SEQ ID NO: |
|---|---|---|---|---|
| p21 | | | | |
| A (−2283) | AGCAGGCTGTGGCTCTGATT | 13 | CAAAATAGCCACCAGCCTCTTCT | 14 |
| B (−1391) | CTGTCCTCCCCGAGGTCA | 15 | ACATCTCAGGCTGCTCAGAGTCT | 16 |
| C (−8) | TATATCAGGGCCGCGCTG | 17 | GGCTCCACAAGGAACTGACTTC | 18 |
| D (+507) | CCAGGAAGGGCGAGGAAA | 19 | GGGACCGATCCTAGACGAACTT | 20 |
| E (+3984) | AGTCACTCAGCCCTGGAGTCAA | 21 | GGAGAGTGAGTTTGCCCATGA | 22 |
| F (+8566) | CCTCCCACAATGCTGAATATACAG | 23 | AGTCACTAAGAATCATTTATTGAGCAC | 24 |
| G (+9985) | CACTGCAATTTGGCCCAGA | 25 | GTGCAGTAGAGAATTATTCCACATTTG | 26 |
| PUMA | | | | |
| A (+1153) | GCGAGACTGTGGCCTTGTGT | 27 | CGTTCCAGGGTCCACAAAGT | 28 |
| B (+2468) | TGTCTGGCTCCGAGTTTGTG | | GGTCAGAAACCCCAACATTCC | 30 |
| C (+6811) | CCCGCATTGCTTGCTTATTAA | | GAGCTTCACCACATGCGTTTC | 32 |
| D (+11430) | GAAGAGCAAATGAGCCAAACG | | GGAGCAACCGGCAAACG | 34 |

Coimmunoprecipitation and RNA-IP

Cells were lysed in cold lysis buffer (50 mM Tris-Cl at pH 7.4, 150 mM NaCl, 1 mM EDTA, 1% NP-40, 0.25% sodium deoxycholate, protease inhibitor mixture). Cell extracts (500 μg) were incubated with the first antibodies or control normal IgG on a rotator overnight at 4° C., followed by addition of protein A/G Sepharose CL-4B beads for 2 h at 4° C. Beads were then washed four times using the lysis buffer. The immune complexes were subjected to SDS-PAGE followed by immunoblotting with the secondary antibody. For RNA-IP experiments, cells were lysed in ice-cold NET-2 buffer (50 mM Tris-HCL at pH 7.4, 300 mM NaCl, 0.5% [vol/vol] Nonidet P-40, 1× complete protease inhibitors [Roche], 100 U/mL RNase OUT [Invitrogen]). The lysate was incubated with the indicated antibodies or control normal rabbit/mouse IgG on a rotator overnight at 4° C., followed by addition of protein A/G agarose (Invitrogen) for 2 h at 4° C. Beads were then washed four times using the NET-2 buffer. Immunoprecipitated RNA was then extracted using Trizol and reverse-transcribed with random hexamers. The resulting cDNA was analyzed with the indicated primer sets (Table 5).

TABLE 5

| Gene | Sense (5'-3') | SEQ ID NO: | Antisense (5'-3') | SEQ ID NO: |
|---|---|---|---|---|
| p21-I | CTTGTGGAGCCGGAGCT | 3 | TGGTGTCTCGGTGACAAAGT | 4 |
| p21-II | GGAGACTCTCAGGGTCGAAA | 35 | GGATTAGGGCTTCCTCTTGG | 36 |
| p21-III (+4008) | CAGAGCAGGCAGGTAGG | 37 | TTTCCCAAGGATGTCGT | 39 |
| p21-IV (+5357) | CCAGGGCCTTCCTTGTATCTCT | 39 | ACATCCCCAGCCGGTTCT | 40 |
| p21-V (+5791) | CTGGAGACTCTCAGGGTCGAA | 41 | CACATGTCCGCACCTGTCAT | 42 |
| p21-VI (+7450) | CCCCACTGTCTTCCTCAGTTG | 43 | AGAAGTCAGCCAGGCCAAGAA | 44 |
| PUMA (S) | TGGCGGACGACCTCAACG | 5 | CCCTGGGTAAGGGCAGGAG | 6 |
| PUMA (Un) | GGTGGTCCCCACTTAGCACA | 45 | GCAATCCTCTGCCACTCCC | 46 |
| GADD45 (S) | TCAGCGCACGATCACTGTC | 7 | CCAGCAGGCACAACACCAC | 8 |
| GADD45 (Un) | CCG GGCAGTGGTTGAGGG | 47 | GGCCAGTGAGCGCAGAAGC | 48 |

TABLE 5 -continued

| Gene | Sense (5'-3') | SEQ ID NO: | Antisense (5'-3') | SEQ ID NO: |
|---|---|---|---|---|
| NOXA (S) | CCGATCCCAGCATCCCT | 49 | GCCGGAAGTTCAGTTTGTCTC | 50 |
| NOXA (Un) | GGAAGTGGTGCATTGCAAATG | 51 | CACACAAGCGCCAGAGACA | 52 |

B. Example 1

SKIP is Essential for p53 Stress-Induced Expression of the p21, but not PUMA, Genes As observed for many essential proteins, depletion of SKIP by siRNA increases endogenous p53 levels. Immunoblot analysis of extracts from SKIP-depleted U2OS cells revealed a significant increase in the steady-state level of p53, which was phosphorylated at Ser15, a modification that stabilizes the protein. Levels of the PUMA protein were also elevated, indicating that the induced p53 protein is transcriptionally active. However, p21 protein levels were markedly reduced in SKIP knockdown cells compared with cells expressing a control siRNA. To assess whether SKIP plays a role in the normal p53 stress response, endogenous p53 was induced in two human cancer cell lines, U2OS (osteosarcoma) and HCT116 (colon cancer), using the chemotherapeutic DNA damage agents etoposide (U2OS cells) or doxorubicin (HCT116 cells). DNA damage-induced accumulation of p53 and two of its target genes, p21 and PUMA, was observed in both U2OS (FIG. 1A) and HCT116 (FIG. 1B) cells. Interestingly, p53 levels increased in siRNA-mediated SKIP knockdown cells, and rose further upon exposure of these cells to etoposide or doxorubicin. Consequently, PUMA expression was elevated in SKIP-depleted cells, and increased further with DNA damage (FIG. 1). In contrast, both basal and stress-induced p21 mRNA levels decreased in SKIP-depleted HCT116 or U2OS cells, compared with cells treated with a control siRNA, accompanied by a strong block to p21 protein expression, as detected by immunoblot (FIG. 1A, 1B, lanes 1-3 and 4-6). Similar results were obtained using two different SKIP siRNAs. Taken together, these data show that SKIP is critical for p53 induction of the anti-apoptotic gene target p21, but not for the proapoptotic PUMA gene.

C. Example 2

SKIP is Dispensable for Stress-Induced Transcription of the p21 Gene

Figure 2:
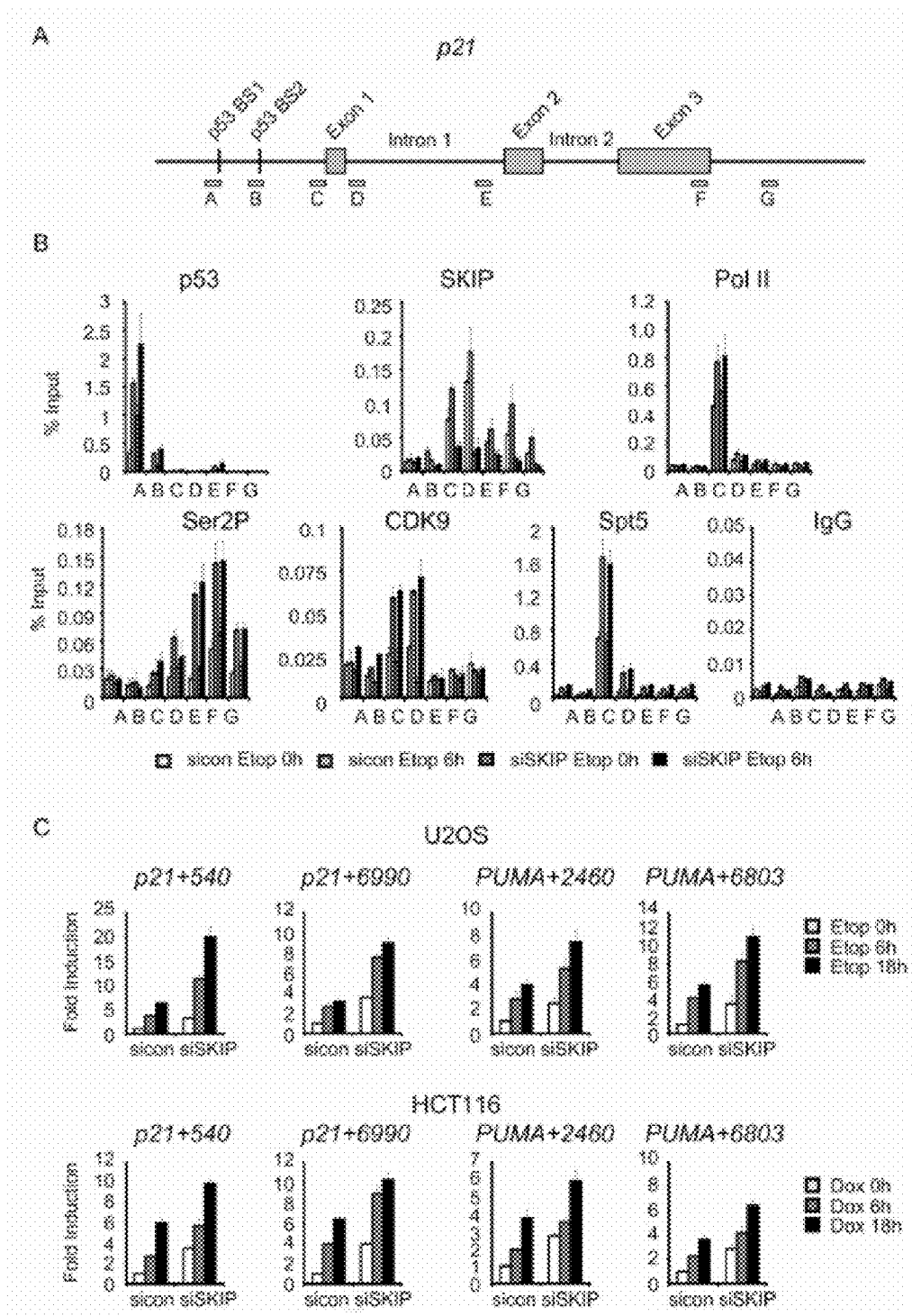
FIG. 2. Loss of SKIP does not affect the p21 gene transcription. (A) Schematic representation of the p21 gene locus, and the relative locations of the primers used for ChIP. (B) ChIP analysis in U2OS cells transfected with control or SKIP siRNA for 48 h, followed by vehicle or etoposide (20 μM) for a further 6 h. ChIP-enriched DNA was quantified by qPCR with the indicated primers, and values are expressed as percentage of input DNA. Error bars represent the standard deviation obtained from three independent experiments. (C) qRT-PCR analysis of p21 and PUMA primary transcripts. U2OS cells (top) or HCT116 cells (bottom) were transfected with control or SKIP siRNA, and incubated with etoposide (top) or doxorubicin (bottom) for the indicated times. Numbers of the primers indicate the position of the first base pair relative to the transcription start site. The mRNA expression levels were normalized to GAPDH. Error bars represent the standard deviation obtained from three independent experiments.

It was surprising to find a role for SKIP in the p53 pathway, because other elongation factors, including P-TEFb and FACT, are dispensable for p21 expression under conditions of stress. Consequently, RNAi chromatin immunoprecipitation (RNAi-ChIP) experiments were used to examine the block to p21 expression in SKIP-depleted U2OS cells before and after exposure to etoposide at the promoter and throughout the coding region (FIG. 2A). The ChIP experiments revealed increased p53 binding to the p21 promoter in SKIP knock-down cells, consistent with the observation that p53 is induced in these cells, and p53 occupancy at the gene increased further following etoposide treatment (FIG. 2B). ChIP analysis of the PUMA gene revealed a similar increase in p53 binding in cells treated with SKIP siRNA, which increased further upon stress induction. Therefore, the loss of p21 protein expression in SKIP-depleted cells is not due to impaired binding of p53 to its target genes.

Further ChIP analysis revealed that SKIP is present at the p21 gene in the absence of stress, with the highest levels at the promoter and proximal downstream region, but it is also present at lower levels in the coding region, following a pattern similar to that observed for P-TEFb/CDK9. SKIP binding was slightly enhanced by stress and greatly reduced in SKIP knockdown cells (FIG. 2B), consistent with the overall loss of SKIP protein (FIG. 1A). In contrast, only background levels of SKIP were detected at the PUMA gene, and this signal did not change upon SKIP knockdown. Thus, SKIP associates specifically with the p21, and not PUMA, gene promoters. High levels of RNAPII at the p21 core promoter were detected in the absence of stress, indicative of a paused RNAPII complex, whereas RNAPII occupancy was low at the PUMA promoter but increased strongly following etoposide treatment (FIG. 2B). Knockdown of SKIP did not affect recruitment of RNAPII, CDK9, or Spt5 at the stress-induced p21 or PUMA genes. Moreover, Ser2-phosphorylated RNAPII levels were unaffected in SKIP knockdown cells, indicating that SKIP is not required for accumulation of active RNAPII elongation complexes within the transcribed region of the p21 (FIG. 2B) or PUMA genes. Together, the RNAi-ChIP studies indicate that SKIP is selectively recruited the p21 promoter, but is not required for binding of p53 or transcription elongation at the stress-induced p21 gene in vivo.

To confirm that SKIP is not required for transcription under stress conditions, accumulation of nascent unspliced p21 transcripts in SKIP knock-down cells was investigated. Total RNA was isolated from U2OS cells in the presence or absence of etoposide, and was amplified using intron-specific primers specific for nascent p21 and PUMA transcripts. Interestingly, primary transcripts derived from the p21 (+540 and +6990 primers) and PUMA (+2460 and +6803 primers) genes increased significantly in SKIP knock-down U2OS cells in the absence of stress, and even more dramatically upon addition of etoposide (FIG. 2C, top row). Virtually identical results were observed in HCT116 cells following doxorubicin treatment (FIG. 2C, bottom row). No significant signals were detected from control PCR reactions programmed with RNA but lacking reverse transcriptase, indicating that the RNA samples were effectively free of contaminating genomic DNA. SKIP is thus dispensable for stress-induced nascent p21 transcription in vivo.

D. Example 3

SKIP is Required for Pre-mRNA Splicing of p21, but not PUMA, Transcripts

Figure 3:
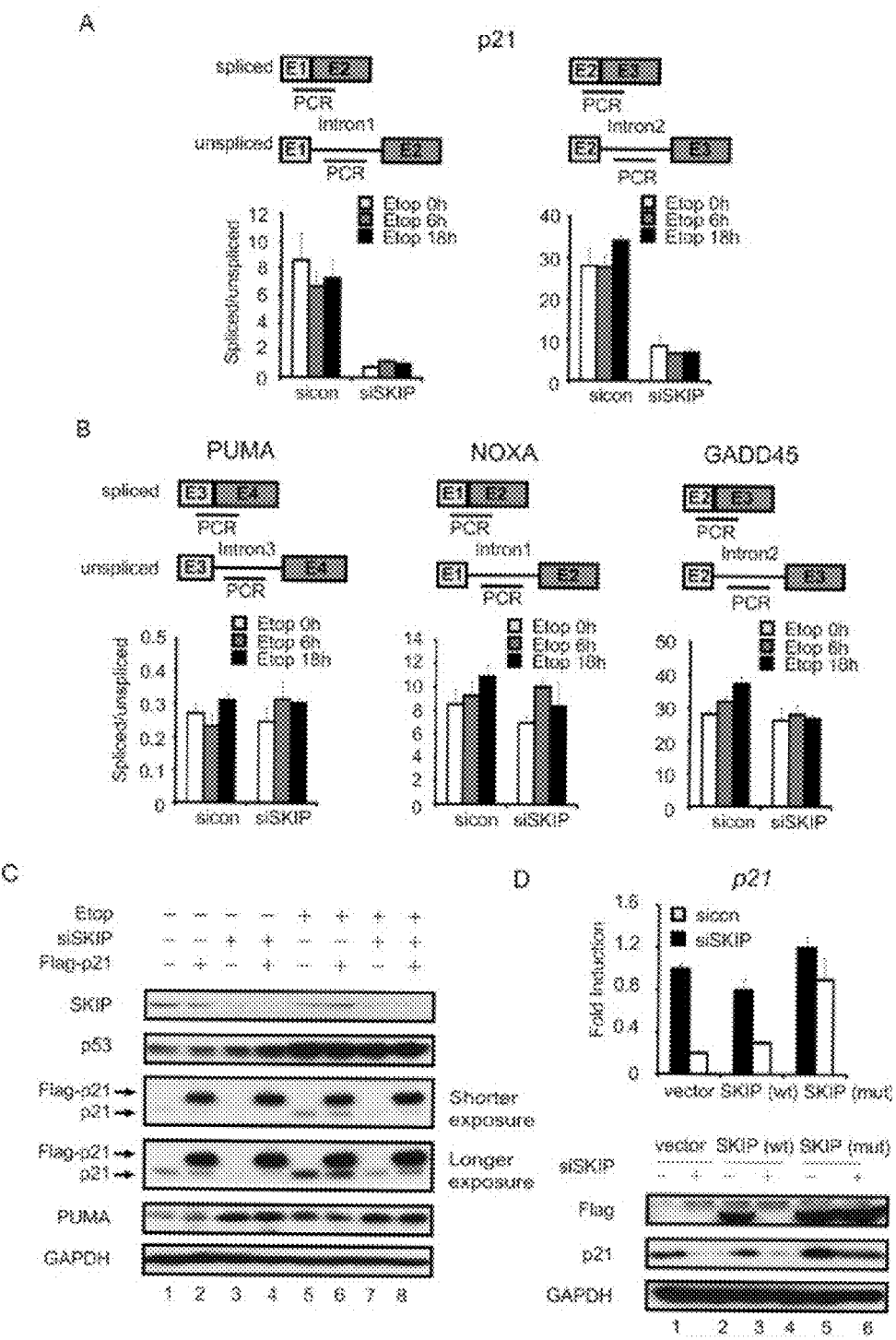
FIG. 3. SKIP regulates p21 mRNA splicing in vivo. (A, top) Schematic diagram of the primer pairs used to detect p21 unspliced and spliced mRNAs. (Bottom) qRT-PCR analysis was used to determine the ratio of unspliced to spliced p21 mRNA. U2OS cells were transfected with control or SKIP siRNA, and incubated with etoposide as indicated. (B) The top panel shows a schematic representation of the primer pairs used to detect the PUMA, GADD45, or NOXA unspliced and spliced mRNAs, whereas the bottom panel shows the ratio of unspliced to spliced mRNA for each gene, as determined by qRT-PCR. U2OS cells were treated as in A. (C) U2OS cells were transfected with empty vector or pCMV-Flag-p21, and, 24 h later, were transfected with control or SKIP siRNA for another 48 h. Cells were left untreated or treated with etoposide (20 μM) for a further 18 h prior to Western blot analysis. (D) Rescue of SKIP knock-down with an siRNA-resistant vector. U2OS cells were transfected with control, wild-type, or mutant SKIP vectors, and, 12 h later, were transfected with control or SKIP siRNA prior to mRNA and protein analysis at 48 h.

To determine whether SKIP is required for splicing of p21 mRNA, quantitative RT-PCR (qRT-PCR) reactions using intron-exon and exon-exon junction-specific primers were carried out to measure spliced and unspliced mRNA levels, and the ratio of spliced:unspliced transcripts was then used to gage splicing efficiency. As shown in FIG. 3A, splicing at either the first or second p21 intron was relatively unchanged upon etoposide treatment in cells treated with a control siRNA, but declined significantly (eightfold and 3.5-fold to four fold, respectively) in SKIP knockdown cells. The drop in splicing efficiency in SKIP knockdown cells was evident in both the presence and absence of DNA damage. Importantly, loss of SKIP did not affect splicing at the PUMA, NOXA, and GADD45 genes, all of which are direct targets of p53 (FIG. 3B). Virtually identical results were obtained in HCTZ 16 cells exposed to doxorubicin. The data show that SKIP is important for efficient splicing of both p21 mRNA introns, but does not affect splicing of PUMA or other tested p53-induced transcripts.

To examine the effects of SKIP knockdown on the p21 mRNA stability, qRT-PCR was performed to measure p21 mRNA half-life in U2OS cells that were transfected with SKIP or control siRNAs for 48 h, followed by treatment with transcriptional inhibitor actinomycin D for 0, 2, 4, or 6 h. The results indicate that SKIP has no significant effect on p21 mRNA stability. The SKIP homolog in *Drosophila* has been shown to promote the export of spliced mRNAs (Farny et al., *Genes Dev* 22:66-78 (2008)). To test whether SKIP affects the mRNA export of p21 mRNA in human cells, SKIP or control siRNAs were transfected in U2OS cells for 48 h, followed by the treatment with etoposide for 18 h. Cells were fractionated into nuclear and cytoplasmic fractions, and mRNA levels were monitored. Depletion of SKIP did not significantly affect export of either p21 or GAPDH mRNAs, indicating that the mRNA export pathway used in mammalian cells under DNA damage conditions is not dependent on SKIP.

To determine whether SKIP might also affect p21 protein stability, the rate of p21 protein turnover was measured in SKIP knockdown cells in the absence of stress. Forty-eight hours after transfection with control or SKIP siRNA, U2OS cells were treated with cycloheximide (CHX) to prevent new protein synthesis, and the decay of endogenous p21 protein was measured. The results indicate that SKIP has no significant effect on p21 stability in the absence of stress. The proteasome inhibitor MG132 elevated p21 protein levels in both control and SKIP siRNA transfected cells, indicating that it is a short-lived protein and subject to active proteolytic degradation under both conditions.

To assess whether cDNA encoding p21 is expressed independently of SKIP in these cells, a Flag-tagged p21 cDNA encoding the full-length p21 protein expressed from a heterologous (CMV) promoter and lacking both introns as well as 5' untranslated region (UTR) and 3'UTR sequences was transfected into U2OS cells, and, after 24 h, either control or SKIP siRNAs were transfected into the cells for a further 48 h, followed by treatment with or without etoposide for 18 h. As shown in FIG. 3C, the basal and stress-induced endogenous p21 protein levels decreased in SKIP-depleted cells, whereas expression of the larger Flag-p21 hybrid protein was unaffected. Similar results were obtained from p53-null H1299 cells in the absence of stress. Importantly, the decrease of p21 mRNA and protein levels in SKIP knockdown cells was effectively rescued upon expression of a vector encoding an siRNA-resistant form of SKIP, but not the wild-type (siRNA-sensitive) SKIP (FIG. 3D), indicating that these results are not due to off-target effects. Together, these data indicate that SKIP regulates p21 expression through a unique gene-specific splicing mechanism.

E. Example 5

SKIP Interacts with and Recruits U2AF65 to the p21 Gene and mRNA

Figure 4:
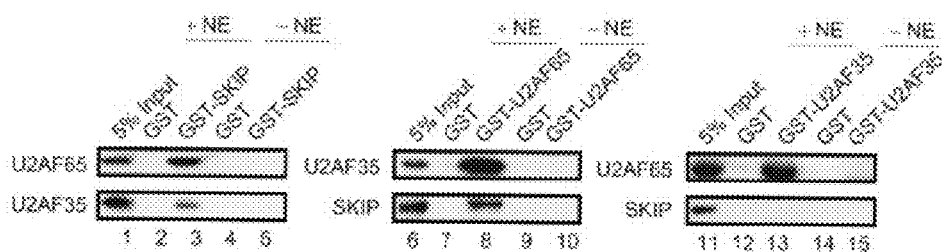
FIG. 4. SKIP associates with unspliced p21 mRNA and recruits U2AF65. (A) Immunoblot analysis of the interaction between SKIP, U2AF35, and U2AF65 in GST pull-down experiments from HCT116 cell nuclear extract. (B) Total proteins were extracted from U2OS cells for coimmunoprecipitation. Immunoprecipitates were examined by Western blot using antibodies against SKIP, U2AF35, or U2AF65. (C) ChIP analysis of U2AF65 binding on the p21 and PUMA genes. U2OS cells were transfected with control or SKIP siRNA for 48 h, followed by treatment with vehicle or etoposide (20 μM) for 6 h. Protein extracts were immunoprecipitated with antibodies against U2AF65. ChIP-enriched DNA was quantified by qPCR with the indicated primers in FIG. 2A. (Right) Immunoblot analysis. Error bars represent the standard deviation obtained from three independent experiments. (D, top panel) Schematic representation of the primer pairs used to detect p21 unspliced and spliced mRNAs. RNA-IP analysis of binding of the SKIP protein to p21 unspliced or spliced mRNA. U2OS cells were transfected with control or SKIP siRNA for 48 h. RNA samples were purified from non-precipitated cellular lysates (input), or extracts precipitated with control IgG or SKIP antibody. Immunoprecipitated p21 mRNA was detected using qRT-PCR with the indicated primers. Values were expressed as percentage of input RNA. Error bars represent the standard deviation obtained from three independent experiments. (E) RNA-IP analysis of binding of CBP80 or U2AF65 to p21, PUMA, or GADD45 unspliced or spliced mRNA. Experiments were performed as in D. The primers used for detecting p21 transcripts were primer IV (unspliced) and primer I (spliced) as in D. The primers used for detecting PUMA or GADD45 transcripts were the same as in FIG. 3B.
Figure 4:
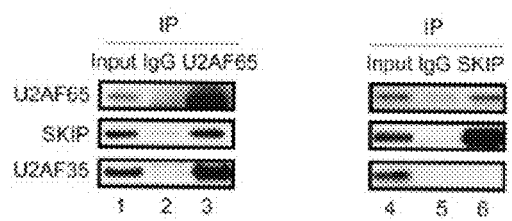
Figure 4:
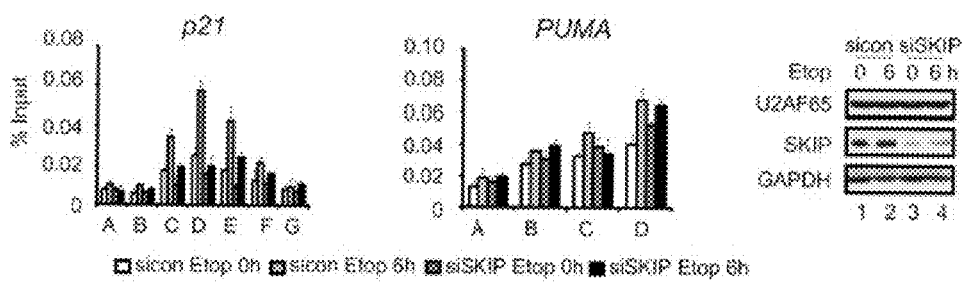
Figure 4:
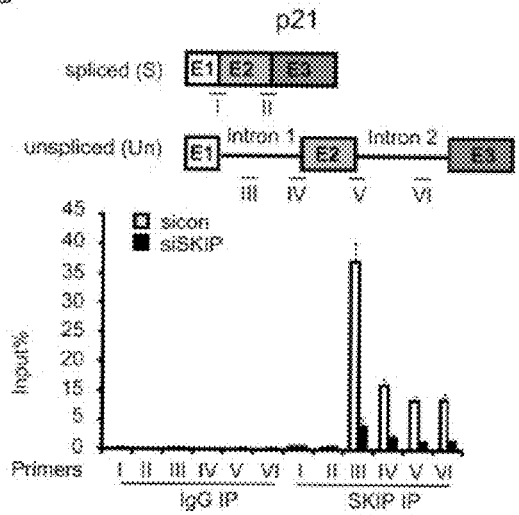
Figure 4:
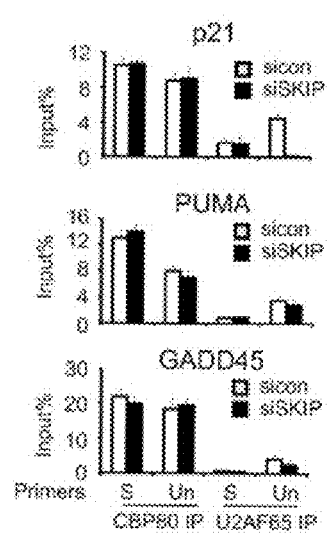

To determine whether human SKIP protein associates with the U2AF complex, recombinant full-length glutathione-S-transferase (GST)-SKIP was purified and coupled to glutathione-S-sepharose beads for GST pull-down experiments using nuclear extracts from HCT116 cells. Relatively low levels of U2AF35 were recovered in the GST-SKIP pull-down fractions, and this association was disrupted when the beads were treated with RNase A, indicating that this interaction may be indirect. Interestingly, much stronger binding of the endogenous U2AF65 protein to the GST-SKIP beads was observed (FIG. 4A, left panel), and this association was unaffected by RNase A. No U2AF65 was recovered in the control GST bead fraction, indicating that the interaction is specific for SKIP. In reciprocal pull-down experiments, GST-U2AF65 bound avidly to nuclear U2AF35 and SKIP, whereas none of these factors bound to GST alone (FIG. 4A, middle panel, cf. lanes 7 and 8). Interestingly, SKIP was not detected in GST-U2AF35 pull-down fractions (FIG. 4A, right panel), which otherwise contained high levels of nuclear U2AF65. To examine this association further, reciprocal coimmunoprecipitation experiments were performed with U2OS whole-cell lysates. As shown in FIG. 4B, both SKIP and U2AF35 coimmunoprecipitated with U2AF65 (left panel), whereas U2AF65, but not U2AF35, was recovered in the SKIP immunoprecipitate (right panel). The results thus show that SKIP interacts with U2AF65 independently of U2AF35.

Based on these findings, RNAi-ChIP experiments were used to analyze whether SKIP is responsible for cotranscriptional recruitment of mRNA splicing factors at the p21 gene. Interestingly, U2AF65 occupancy within the coding region of the p21 gene decreased significantly in SKIP knockdown cells (FIG. 4C, left panel). In contrast, loss of SKIP had no effect on binding of U2AF65 to the PUMA gene (FIG. 4C, center panel). Steady-state U2AF65 protein levels were unaffected in SKIP-depleted cells, as measured by immunoblot (FIG. 4C, right panel). The results indicate that SKIP is required for stable binding of U2AF65 at the p21, but not PUMA, genes in vivo.

These data strongly suggest that SKIP regulates cotranscriptional loading of U2AF65 and splicing at both introns of the p21 gene, and that spliceosomal complexes formed in the absence of SKIP may be unable to splice p21 mRNAs whether on or off of the gene. To examine U2AF65 binding to p21 mRNA directly, RNA immunoprecipitation (RNA-IP) experiments were carried out in U2OS cell extracts. As shown in FIG. 4D, high levels of the p21 transcript were recovered in SKIP antibody, and not control immunoglobin G (IgG), immunoprecipitates. Importantly, the SKIP immunoprecipitation (SKIP-IP) fractions contained significantly higher levels of unspliced (detected with primers III-VI) than spliced (detected with primers I-II) transcripts. Furthermore, the level of unspliced transcript bound to SKIP declined greatly in SKIP knockdown cells, whereas the low background level of spliced mRNA in the SKIP-IP fraction was unaffected, indicating that this latter signal is nonspecific. The higher signal detected with primer III likely reflects an increased efficiency in binding to p21 mRNA. Interestingly, SKIP also bound to PUMA mRNA introns. Thus, SKIP binds preferentially to introns, presumably as part of the spliceosome complex, but does not discriminate between the p21 and PUMA mRNA.

The results indicate that SKIP selectivity in splicing is conferred by its ability to bind to the core promoter and recruit U2AF65 cotranscriptionally to the p21 gene and mRNA.

Promoter-proximal intron splicing is strongly influenced by 5'-mRNA capping. The effect of SKIP loading of the mRNA cap-binding protein CBP80 was examined. As shown in FIG. 4E, p21, PUMA, and GADD45 mRNAs were efficiently recovered in CBP80 immunoprecipitates, and ablation of SKIP had no affect on CBP80 binding to either the spliced or unspliced mRNAs. In contrast, U2AF65 bound preferentially to the unspliced mRNAs. Most interestingly, the binding of U2AF65 to unspliced p21 mRNA was largely abolished in si-SKIP-treated cells (FIG. 4E), consistent with the ChIP results, whereas U2AF65 binding to the PUMA or GADD45 mRNAs was only modestly affected in SKIP knockdown cells. To assess whether U2AF65 is required for expression of p21 and PUMA genes, mRNA and protein levels for these genes were analyzed in cells transfected with si-U2AF66. Knockdown of U2AF65 significantly reduced pre-mRNA splicing and protein expression of both p21 and PUMA mRNAs in control and DNA-damaged cells, confirming its role as a general splicing factor. These data indicate that SKIP binds to introns at both target and nontarget mRNAs, and is required for binding of U2AF65 to p21 mRNA. Although U2AF65 is also required for splicing of PUMA mRNA, it is recruited to the gene and mRNA independently of SKIP.

F. Example 5

SKIP is Required for p21 Induction by Nutlin3a or TGF-β Signaling

Figure 5:
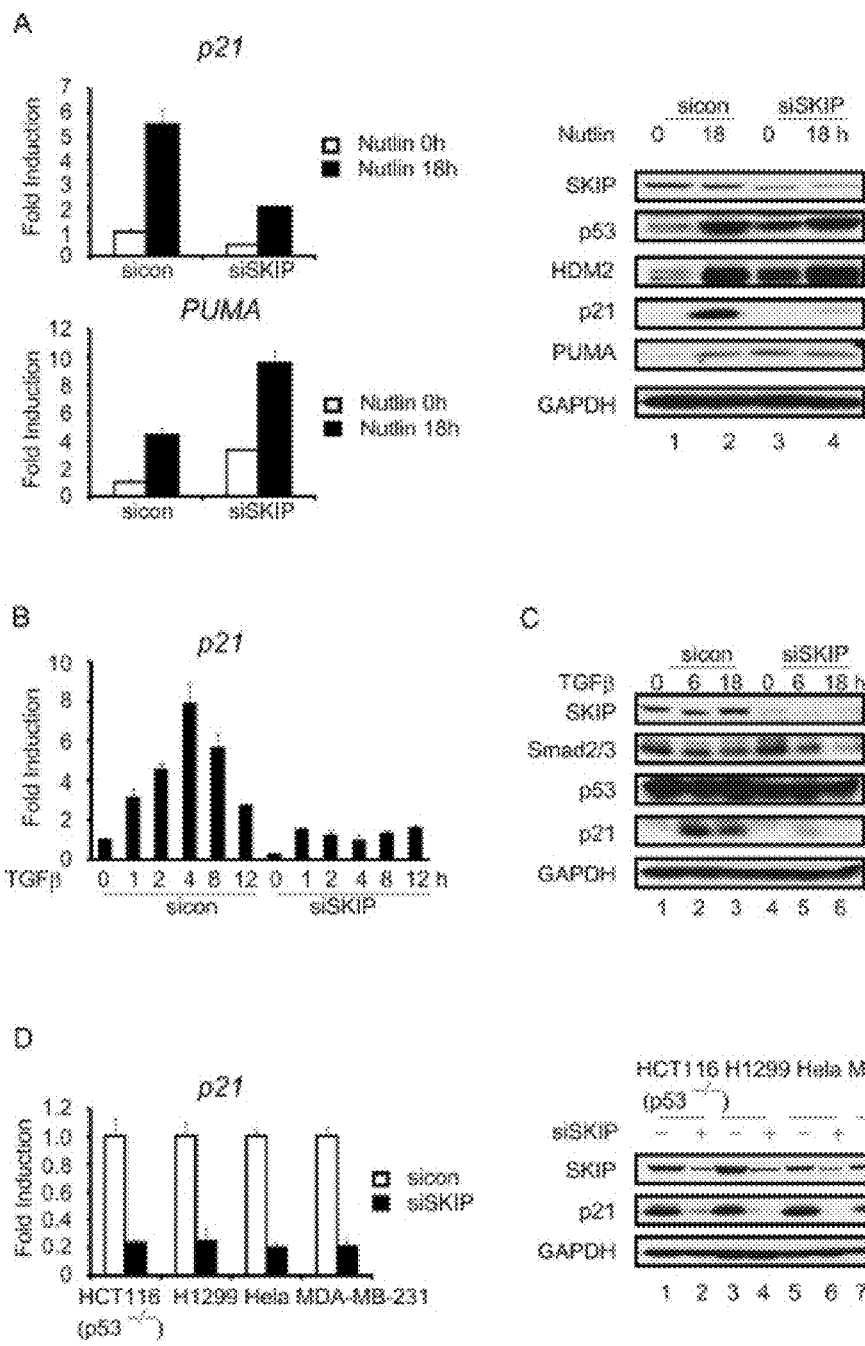
FIG. 5. SKIP is required for Nutlin and TGF-β-induced p21 gene expression. (A, left) qRT-PCR analysis of p21 and PUMA mRNA levels. U2OS cells were transfected with control or SKIP siRNA for 48 h, and incubated in the presence or absence of Nutlin (10 μM) for 18 h. (Right, lanes 1-4) Protein lysates were subjected to immunoblot analysis. (B) qRT-PCR analysis of p21 mRNA levels. MDA-MB-231 cells were transfected with control or SKIP siRNA for 48 h, followed by incubation in the presence or absence of TGF-β (5 ng/mL) for the indicated times. (C, lanes 1-6) Immunoblot analysis of SKIP, Smad2/3, p53, p21, or GAPDH in cells transfected with control or SKIP siRNA for 48 h, followed by treatment with TGF-β (5 ng/mL) for the indicated times. (D, left) qRT-PCR analysis of p21 mRNA levels in HCT 116 p53$^{-/-}$ cells, H1299 cells, HeLa cells and MDA-MB-231 cells transfected with control or SKIP siRNA for 48 h. (Right, lanes 1-8) Protein lysates were subjected to immunoblot analysis. All of the mRNA expression levels were normalized to GAPDH mRNA, and are represented as fold increase or decrease over untreated cells. Error bars represent the standard deviation obtained from three independent experiments.

To assess whether SKIP-regulated p21 gene expression is restricted to conditions of stress, the nongenotoxic drug Nutlin3 was used to activate p53 and induce p21 gene expression in U2OS cells. Nutlin3 disrupts binding of p53 to the HDM2 ubiquitin ligase, and therefore can stabilize p53 in the absence of stress. As shown in FIG. 5A, Nutlin3 induced p53 activation of several downstream target genes, including p21, PUMA, and HDM2. Nutlin3-induced expression of PUMA and HDM2 was further increased in si-SKIP cells, while the induction of p21 was strongly suppressed. Thus, SKIP is required for p53-induced p21 expression, irrespective of DNA damage.

To address whether SKIP regulation depends on the activator, p21 induction was studied in the human breast cancer cell line MDA-MB-231, which expresses a mutant p53 protein, treated with anti-mitogenic cytokine transforming growth factor-β (TGF-β). In these cells, p21 mRNA was induced rapidly in response to TGF-β signaling, and mRNA levels peaked 4 h after induction (FIG. 5B). Addition of TGF-β did not affect the mutant p53 protein levels (FIG. 5C). Strikingly, this increase of p21 mRNA and protein was completely abolished in SKIP knockdown cells (FIG. 5B,C). These findings in H1299 (p53-null) cells were compared with two cell lines that are deficient for p53 signaling: HeLa (p53 inactivated by the E6 protein of HPV-18) and HCT 116 p53$^{-/-}$ (p53 gene deleted by homologous recombination). In all of these cells, loss of SKIP gave rise to a strong inhibition of endogenous p21 mRNA and protein expression (FIG. 5D). The data indicate that, in the absence of stress, SKIP affects both p21 transcription elongation and splicing. Together, these findings highlight the general role for SKIP as a critical regulator of p21 expression.

G. Example 6

Figure 6:
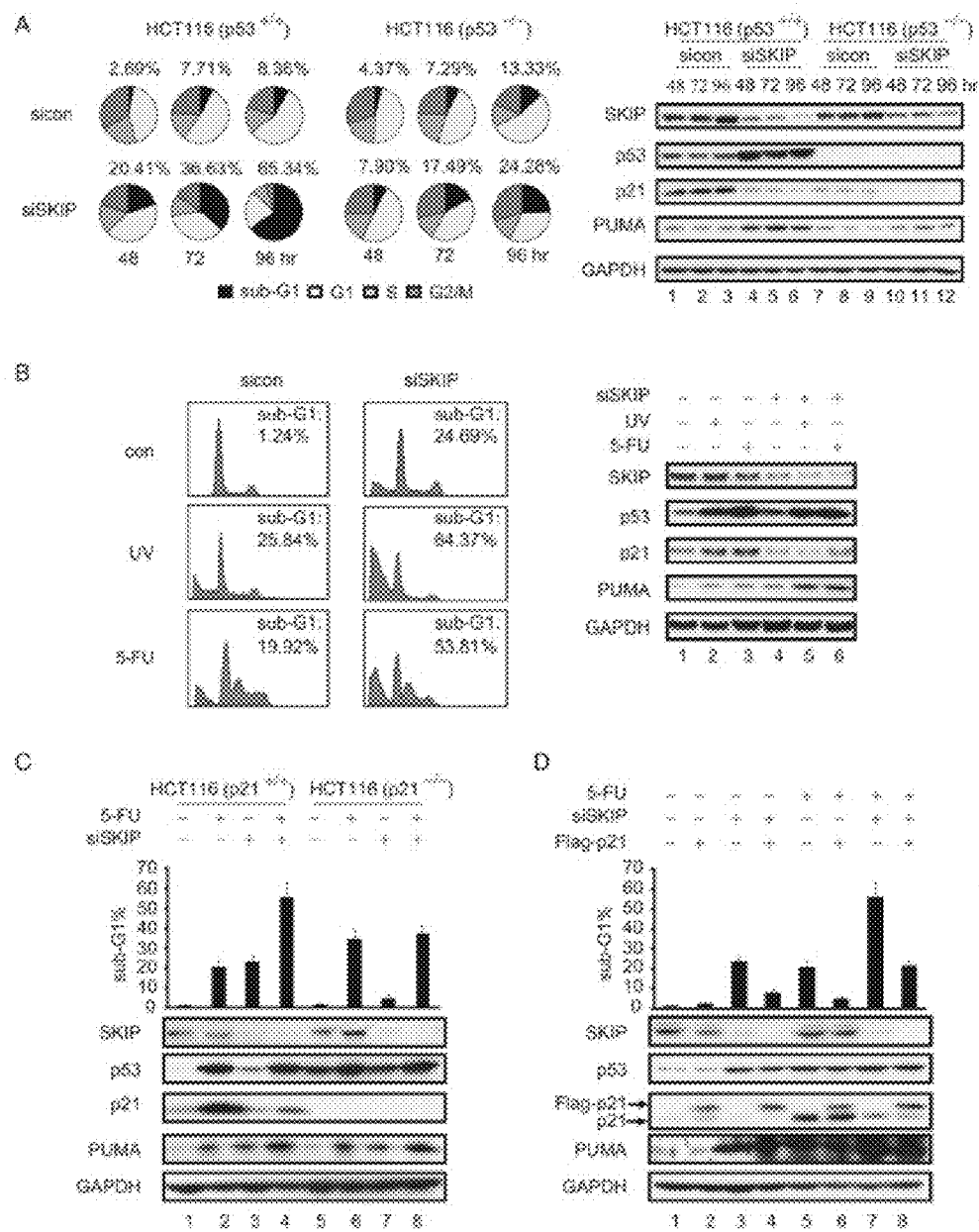
FIG. 6. SKIP1 is required for cell survival and modulates DNA damage-induced cell apoptosis. (A, left) FACS analysis of the cell cycle profile. HCT116 cells or HCT116 p53$^{-/-}$ cells were harvested at indicated times after transfection with control or SKIP siRNA, and the DNA content was determined by FACS. Pie charts display the percentage of cells in each stage of the cell cycle. The percentage of sub-G1 cells is indicated above each chart. (Right) Cell extracts were subjected to immunoblot analysis. (B, left) FACS analysis of cell apoptosis. Twenty-four hours after control or SKIP siRNA transfection, HCT116 cells were left untreated or treated with UV (60 J/m$^2$) or 5-FU (50 μM) for 24 h. The percentage of cells in the sub-G1 phase was quantified for the plots. (Right, lanes 1-6) Cell extracts were subjected to immunoblot analysis. Role of p21 in SKIP-regulated cell apoptosis. (C, top) FACS analysis of cell apoptosis. HCT116 cells or HCT116 p21$^{-/-}$ cells were transfected with control or SKIP siRNA for 24 h, and left untreated or treated with 5-FU (50 μM) for 24 h. FACS was performed as in FIG. 6. The percentage of cells in the sub-G1 phase was quantified and is represented in the graph. (Bottom, lanes 1-8) Cell extracts were subjected to immunoblot analysis. (D, top) FACS analysis of cell apoptosis. HCT116 cells were first transfected with empty vector or pCMV-Flag-p21, and, 24 h later, were transfected with control or SKIP siRNA for another 24 h, and then the cells were left untreated or treated with 5-FU (50 μM) for a further 24 h. The percentage of cells in the sub-G1 phase was quantified and is represented in the graph. (Bottom, lanes 1-8) Cell extracts were subjected to immunoblot analysis. Error bars represent the standard deviation obtained from three independent experiments.

SKIP is an Essential Cancer Cell Survival Factor that Counteracts DNA Damage-Induced Apoptosis The observation that SKIP is critical for p21, but not PUMA, gene expression indicates that loss of SKIP predisposes cells to undergo p53-dependent apoptosis. To test this directly, HCT116 cells were transfected with SKIP siRNA or control siRNA for 48, 72, and 96 h. The cells were collected and the percentage of cells in each phase of the cell cycle was quantified by flow cytometric analyses. As shown in FIG. 6A, knockdown of SKIP did not lead to cell cycle arrest at the G1, S, or G2/M phase of the cell cycle. Rather, the SKIP-depleted cells were subjected to massive DNA fragmentation and cell apoptosis, as measured by the sub-G1 DNA content, with >70% cell death at 96 h following transfection of SKIP siRNA. Next, we asked whether SKIP depletion can induce apoptosis in the isogenic HCT116 p53$^{-/-}$ cell line. As observed in the HCT116 parental cells, the cell cycle progression of the SKIP-depleted cells is similar to that of the cells transfected with control siRNA. However, cell death triggered by knockdown of SKIP is largely attenuated, but not absent, in the HCT116 p53$^{-/-}$ cells, with the percentage of cells in the sub-G1 fraction reduced to 25% after 96 h of treatment with SKIP siRNA (FIG. 6A, bottom panel). The expression of endogenous SKIP was identical in these two cell lines, whereas both p21 and PUMA protein levels were higher in the HCT116 parental cells compared with the p53-null cells (FIG. 6A, right panel). Detailed quantification of the effect of SKIP siRNA on the cell cycle is presented in Table 6. SKIP is thus required for cancer cell survival through its role in p21 expression, which counteracts p53-mediated apoptosis.

TABLE 6

| HCT116 (p53) | | | | | | | |
|---|---|---|---|---|---|---|---|
| | sicon | | | siSKIP | | | |
| | 48 h | 72 h | 96 h | | 48 h | 72 h | 96 h |
| sub-G1 | 2.69 | 7.71 | 8.36 | sub-G1 | 20.41 | 36.63 | 65.34 |
| G1 | 43.61 | 52.02 | 56.47 | G1 | 42.62 | 35.80 | 21.60 |
| S | 20.98 | 16.43 | 14.84 | S | 16.66 | 12.17 | 8.12 |
| G2/M | 32.72 | 23.84 | 20.33 | G2/M | 20.31 | 15.40 | 4.94 |
| HCT116 (p53) | | | | | | | |
| | sicon | | | siSKIP | | | |
| | 48 h | 72 h | 96 h | | 48 h | 72 h | 96 h |
| sub-G1 | 4.37 | 7.29 | 13.33 | sub-G1 | 7.90 | 17.49 | 24.28 |
| G1 | 46.47 | 47.87 | 54.66 | G1 | 48.53 | 40.77 | 32.29 |
| S | 19.41 | 20.88 | 12.68 | S | 18.46 | 13.17 | 13.93 |
| G2/M | 29.75 | 23.96 | 19.33 | G2/M | 25.11 | 28.57 | 29.50 |

The observation that SKIP remains essential for protein expression even under conditions of stress led to investigation of whether loss of SKIP sensitizes cells to apoptosis induced by chemotherapeutic DNA damage agents. Therefore, HCT 116 cells were treated either with control or SKIP siRNA, and, 48 h after transfection, the cells were treated with UVC or 5-FU for a further 24 h. FACS analysis of these cells revealed that apoptosis induced by UVC or 5-FU treatment was much higher in cells containing reduced levels of SKIP (FIG. 6B, left panel). Immunoblots were also used to monitor the protein levels of SKIP, p53, PUMA, and p21 in these experiments (FIG. 6B, right panel), and confirmed that p21 expression remains SKIP-dependent under UVC and 5-FU stress conditions. These findings indicate that SKIP loss strongly augments chemotherapy-induced cell killing.

The converse, i.e., whether ectopic expression of SKIP would render cells resistant to p53-mediated apoptosis, was also investigated. To address this question, HCT 116 cells were engineered to stably express a VS-tagged SKIP protein (HCT116-SKIP). HCT116 and HCT116-SKIP cells were treat with either UVC or 5-FU for 48 h, and apoptosis was monitored by FACS sorting. Strikingly, HCT116-SKIP cells were much more resistant to DNA damage-induced cell death. Immunoblot analysis of protein expression in these cells indicates that activation of p53 is significantly impaired in these cells, and, consequently, the mechanism is distinct from that observed in SKIP knockdown cells. Similar results were observed in HCT116 cells that overexpress SKIP through transient expression. The data indicate that excessively high levels of SKIP may inactivate factors that are normally required for p53 activation. Taken together, these results suggest that SKIP is critical for cell viability, and that changes in SKIP expression can strongly modulate the cell response to DNA damage.

H. Example 7

The Anti-Apoptotic Function of SKIP is Primarily Due to Its Ability to Regulate p21 Expression The results show that SKIP depletion sensitizes cells to undergo apoptosis through its ability to prevent p21 expression. To test this model, we asked whether knockdown of SKIP affects apoptosis in HCTI 16 p21$^{-/-}$ cells, which lack the p21 protein and are more prone to undergo apoptosis in response to DNA damage. Although p53 was induced more strongly in 5-FU-treated HCT116 cells, levels of the anti-apoptotic p21 protein were also much higher than in these cells than in the SKIP knockdown cells (FIG. 6C, lanes 2 and 3), and consequently, the overall extent of apoptosis was comparable in 5-FU and SKIP-depleted cells. Knockdown of SKIP in the 5-FU-treated cells resulted in high levels of p53 and low levels of p21, further enhancing apoptosis (FIG. 6C, lane 4). In contrast, in the HCT116 p21$^{-/-}$ cells, basal p53 levels are higher (FIG. 6C, lane 5), and increase further upon exposure to 5-FU (FIG. 6C, lane 6), but only modestly, if at all, in the si-SKIP-treated cells (FIG. 6C, lane 7). Consequently, 5-FU treatment increases apoptosis more readily in HCT116 p21$^{-/-}$ cells (FIG. 6C, lane 6), whereas apoptosis is only modestly increased upon SKIP depletion (FIG. 6C, lane 7), consistent with the fact p53 levels are only marginally increased in these cells. Moreover, 5-FU-mediated apoptosis was not enhanced further by SKIP knockdown in the HCT p21$^{-/-}$ cells (FIG. 6C, lane 8). Thus, the enhanced apoptosis seen in SKIP-depleted cells is predominantly linked to down-regulation of p21 expression, which appears to be a major target for SKIP in HCT116 cells, whereas 5-FU-induced cell death is linked to the strong induction of p53.

In addition, we asked whether overexpression of Flag p21 could block the apoptotic effect of SKIP knockdown in HCT116 cells. As shown in FIG. 6D, expression of the Flag-p21 protein significantly reduced cell death induced by depletion of SKIP (lanes 3 and 4) or treatment with 5-FU (lanes 5 and 6), as well as the enhanced level of apoptosis observed in cells exposed to both 5-FU and SKIP-siRNA (lanes 7 and 8). The expression of SKIP, p53, and PUMA under these different experimental conditions was monitored by immunoblot (FIG. 6D, bottom panel), and confirmed that ectopic p21 blocks apoptosis without influencing expression of any of these factors, presumably through induction of cell cycle arrest. Together, these findings show that primary mechanism by which SKIP controls p53 apoptosis is through its ability to regulate p21 expression.

I. Example 8

The SKIP-Associated Factors DHX8, Prp19, and PPIL1 are also Selectively Required for p21 Splicing Although SKIP has been shown to regulate the catalytic step in splicing as a component of the activated spliceosome, our findings indicate that it also functions at an earlier step to regulate loading of U2AF65 at the p21 gene. Consequently, control of other SKIP-interacting splicing factors over p21 gene-specific splicing was investigated. Previous studies have shown that SKIP interacts with DHX8 (hPrp22), the human homolog of a yeast RNA helicase (Gahura et al., *J Cell Biochem* 106:139-151 (2009); Kittler et al., Nature 432: 1036-1040 (2004)). Within the spliceosome, SKIP also associates with Prp 19 complex proteins (Wahl et al., *Cell* 136: 701-718 (2009)).

Surprisingly, we have also found that SKIP interacts with p53 and PPIL1 (peptidyl-prolyl cis/trans isomerase 1). PPIL1 carries out cis-trans isomerization of the peptide bond on the NH$_2$-terminal side of Pro residues, forming a tight bend in the polypeptide backbone that substantially changes the conformation of the protein. Through this isomerization and consequent conformational change, peptidyl-prolyl isomerases alter the functions of target proteins, in this case, likely p53 (Shaw et al. (2002) *EMBO Rep.* 3:521-26).

Figure 7A:
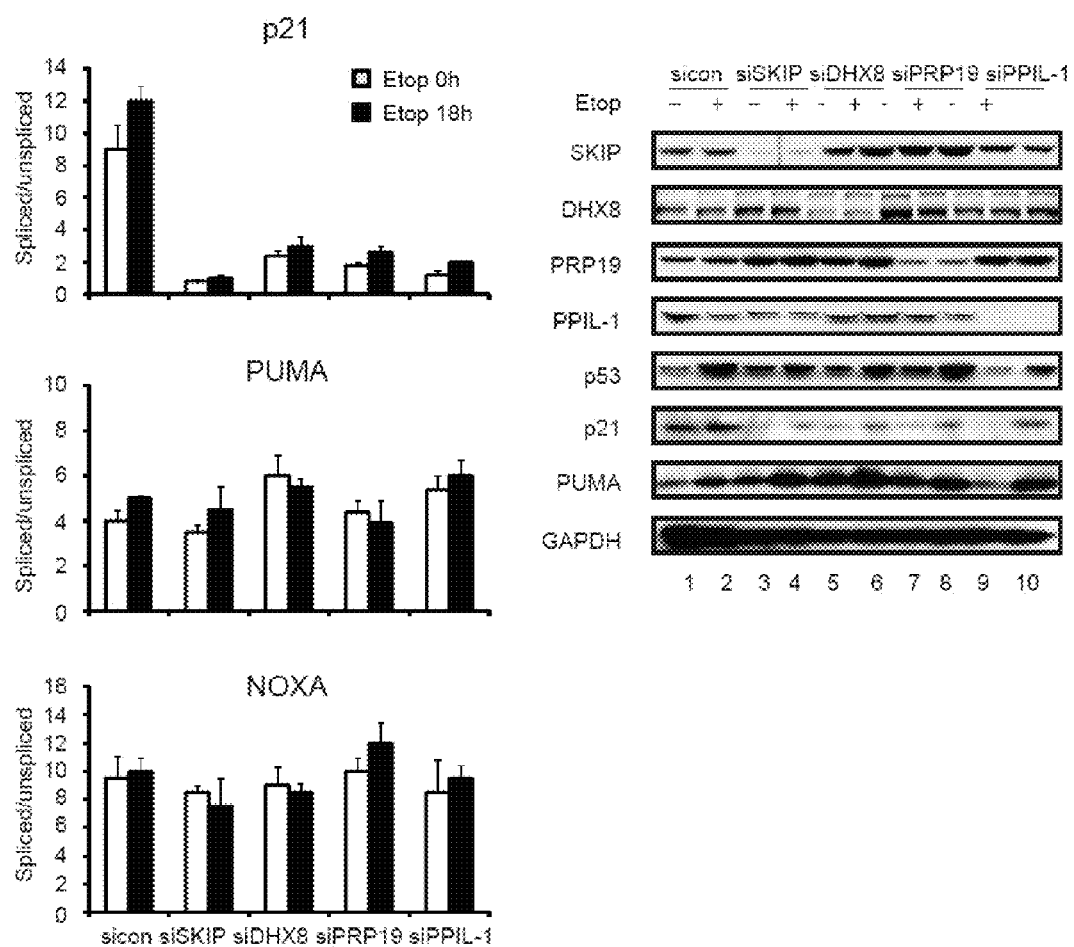
FIG. 7. DHX8, PPIL1, and Prp19 selectively regulate p21 mRNA splicing and protein expression, and DHX8, like SKIP, is required for binding of U2AF65 to p21 unspliced mRNA. (A, left) qRT-PCR was used to monitor the ratio of unspliced to spliced p21, PUMA, or NOXA mRNAs. U2OS cells were transfected with control, SKIP, DHX8, Prp19, or PPIL1 siRNA for 48 h, and incubated in the presence or absence of etoposide (20 μM) for the indicated times. (Right, lanes 1-6). Protein lysates were subjected to immunoblot analysis. (B) RNA-IP analysis of binding of U2AF65 to p21 or PUMA unspliced or spliced mRNA. U2OS cells were transfected with control, SKIP, or DHX8 siRNA for 48 h. RNA samples were purified from non-precipitated cellular lysates (input) or extracts precipitated with U2AF65 antibody. Immunoprecipitated p21 transcript was detected using qRT-PCR with the primers used in FIG. 4E. Values are expressed as percentage of input RNA. Error bars represent the standard deviation obtained from three independent experiments. (C) Model for the role of SKIP in the regulation of p21 gene-specific splicing.
Figure 7B:
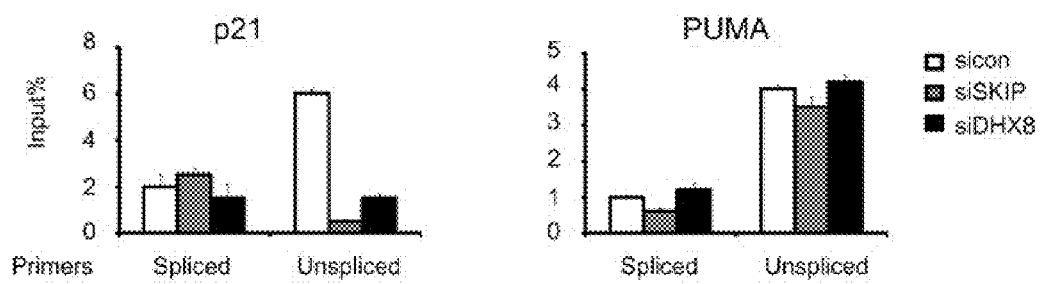
Figure 7C:
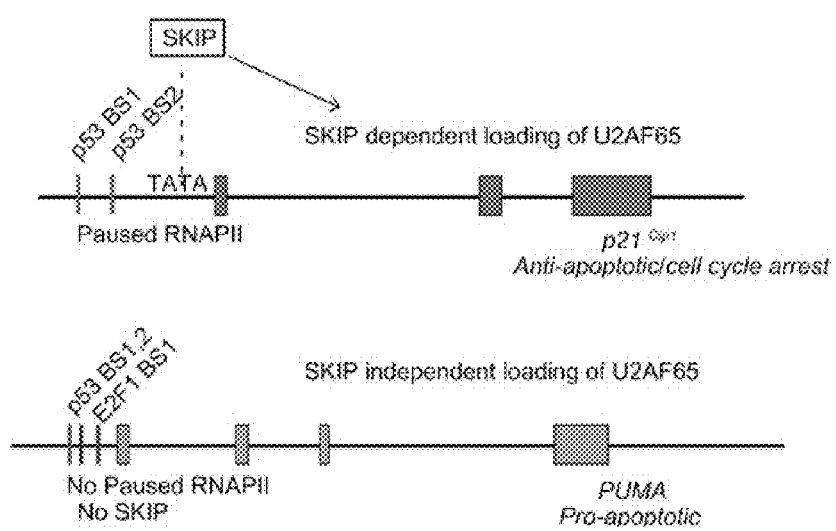

The results revealed that siRNA-mediated knockdown of human DNX8, Prp 19, or PPIL1 leads to a selective down-regulation of splicing of p21 transcripts, without affecting splicing of PUMA or NOXA mRNAs (FIG. 7A, left panel) corresponding decline in p21 protein expression was also evident by immunoblot (FIG. 7A, right panel). Moreover, RNA-IP analysis established that U2AF65 loading on p21 mRNA is strongly reduced in the DHX8 knockdown cells (FIG. 7B). These findings show that other spliceosome components also function selectively in p21 expression, and contrast with siRNA knockdown of U2AF65, which disrupts splicing of both p21 and PUMA mRNAs. Thus, a subset of SKIP-associated spliceosomal proteins is not universally required for splicing under stress, but rather functions in agene-specific manner to regulate cotranscriptional p21 mRNA splicing.

J. Example 9

Expression of SKIP Protein is Highly Sensitive to Flavopiridol

Figure 8:
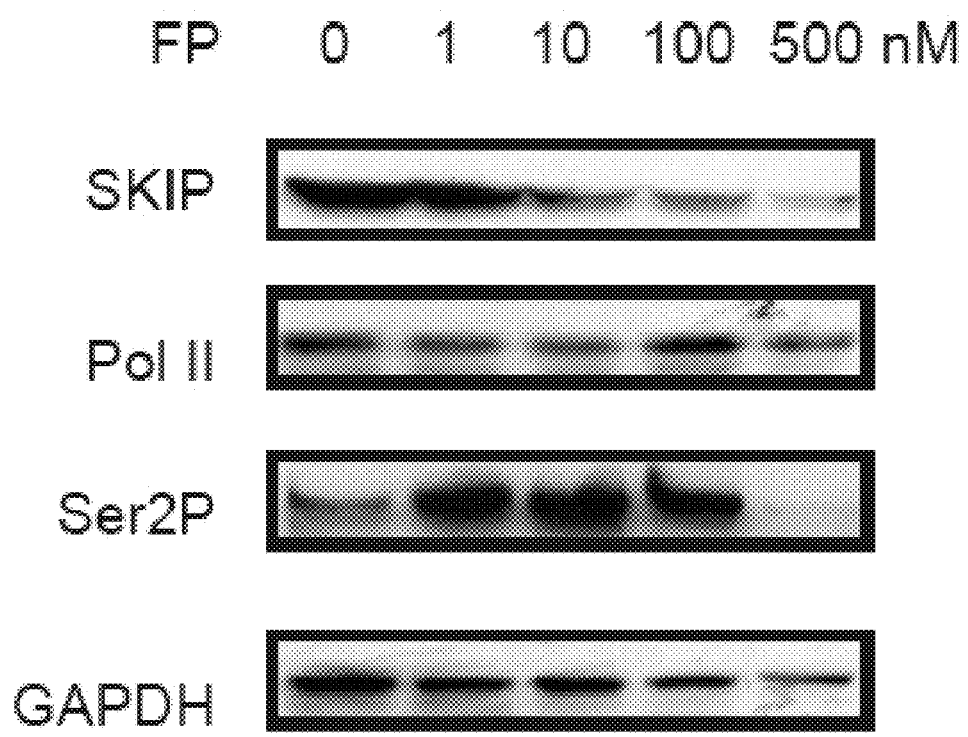
FIG. 8. Immunoblot detection of SKIP and Ser2-phosphorylated RNAPII in response to increasing levels of flavopiridol.

SKIP expression is blocked by Flavopiridol (FP), a CDK inhibitor currently in clinical trials. FIG. 8 shows an immunoblot analysis of endogenous SKIP protein levels in 293 cells exposed for 18hr to FP. SKIP protein levels decline starting at lOnM FP, though mRNA levels are unaffected at 10 nM FP.

In contrast, levels of Ser2-phosphorylated RNAPII decline with exposure to much higher concentrations of FP (>100 nM). These data indicate that SKIP expression is highly sensitive to FP, thus providing a valuable therapeutic option for increasing apoptosis in cancer cells.

Informal Sequence Listing:

(SEQ ID NO: 1)
MALTSFLPAPTQLSQDQLEAEEKARSQRSRQTSLVSSRREPPPYGYRKG
WIPRLLEDFGDGGAFPEIHVAQYPLDMGRKKKMSNALAIQVDSEGKIKY
DAIARQGQSKDKVIYSKYTDLVPKEVMNADDPDLQRPDEEAIKEITEKT
RVALEKSVSQKVAAAMPVRAADKLAPAQYIRYTPSQQGVAFNSGAKQRV
IRMVEMQKDPMEPPRFKINKKIPRGPPSPPAPVMHSPSRKMTVKEQQEW
KIPPCISNWKNAKGYTIPLDKRLAADGRGLQTVHINENFAKLAEALYIA
DRKAREAVEMRAQVERKMAQKEKEKHEEKLREMAQKARERRAGIKTHVE
KEDGEARERDEIRHDRRKERQHDRNLSRAAPDKRSKLQRNENRDISEVI
ALGVPNPRTSNEVQYDQRLFNQSKGMDSGFAGGEDEIYNVYDQAWRGGK
DMAQSIYRPSKNLDKDMYGDDLEARIKTNRFVPDKEFSGSDRRQRGREG
PVQFEEDPFGLDKFLEEAKQHGGSKRPSDSSRPKEHEHEGKKRRKE

What is claimed is:

1. A method of treating colon cancer in an individual comprising: administering to the individual an effective amount of an anti-SKIP siRNA, thereby treating colon cancer in the individual.

2. The method of claim 1, further comprising treating the individual with a DNA damaging agent.

3. The method of claim 2, wherein treatment with the DNA damaging agent is before or concurrent with said administering.

4. The method of claim 2, wherein the DNA damaging agent is a chemotherapeutic agent or radiotherapy.

5. The method of claim 1, wherein the inhibitor of SKIP is flavopiridol.

6. A method of selectively inducing apoptosis in a colon cell comprising: contacting the colon cell with an anti-SKIP siRNA, thereby selectively inducing apoptosis in a colon cell.

7. The method of claim 6, further comprising treating the colon cell with a DNA damaging agent.

8. The method of claim 7, wherein treatment with the DNA damaging agent before or concurrently with the contacting.

9. The method of claim 6, wherein the colon cell forms part of a colon tumor.

10. The method of claim 6, wherein the inhibitor of SKIP is flavopiridol.

11. The method of claim 6, wherein the colon cell is in an individual.

12. The method of claim 11, wherein the individual has colon cancer.

* * * * *